(12) United States Patent
Orr et al.

(10) Patent No.: US 10,973,812 B2
(45) Date of Patent: Apr. 13, 2021

(54) ATAXIA THERAPEUTIC COMPOSITIONS AND METHODS

(71) Applicants: REGENTS OF THE UNIVERSITY OF MINNESOTA, Minneapolis, MN (US); Baylor College of Medicine, Houston, TX (US)

(72) Inventors: Harry T. Orr, Minneapolis, MN (US); Emily A. L. Wozniak, Minneapolis, MN (US); Huda Y. Zoghbi, Houston, TX (US)

(73) Assignees: Regents of the University of Minnesota, Minneapolis, MN (US); Baylor College of Medicine, Houston, TX (US)

( * ) Notice: Subject to any disclaimer, the term of this patent is extended or adjusted under 35 U.S.C. 154(b) by 690 days.

(21) Appl. No.: 15/449,257

(22) Filed: Mar. 3, 2017

(65) Prior Publication Data
US 2017/0252334 A1    Sep. 7, 2017

Related U.S. Application Data

(60) Provisional application No. 62/303,122, filed on Mar. 3, 2016.

(51) Int. Cl.
| | | |
|---|---|---|
| A61K 31/4704 | (2006.01) |
| A61K 9/00 | (2006.01) |
| A61K 9/10 | (2006.01) |
| A61K 47/02 | (2006.01) |
| A61K 38/07 | (2006.01) |

(52) U.S. Cl.
CPC ........ *A61K 31/4704* (2013.01); *A61K 9/0024* (2013.01); *A61K 9/10* (2013.01); *A61K 38/07* (2013.01); *A61K 47/02* (2013.01)

(58) Field of Classification Search
None
See application file for complete search history.

(56) References Cited

U.S. PATENT DOCUMENTS

| | | |
|---|---|---|
| 6,380,230 B1 | 4/2002 | Brodin |
| 2011/0124652 A1 | 5/2011 | Carpenter |
| 2011/0288011 A1 | 11/2011 | Castaigne |

FOREIGN PATENT DOCUMENTS

| | | |
|---|---|---|
| WO | WO 1999015525 A1 | 4/1999 |
| WO | WO 2008025798 A1 | 3/2008 |
| WO | WO 2010014593 A1 | 2/2010 |
| WO | WO 2010063124 A1 | 6/2010 |

OTHER PUBLICATIONS

Mayo Clinic, Ataxia: Symptoms & Causes, https://www.mayoclinic.org/diseases-conditions/ataxia/symptoms-causes/syc-20355652, accessed Feb. 2, 2018 (Year: 2018).*
Mayo Clinic, Ataxia: Diagnosis & Treatment, https://www.mayoclinic.org/diseases-conditions/ataxia/diagnosis-treatment/drc-20355655, accessed Feb. 2, 2018 (Year: 2018).*
Chemical Abstracts Service Registry No. 130408-77-4, accessed Feb. 2, 2018 (Year: 2018).*
Asin, "Behavioral effects of A71623, a highly selective CCK-A agonist tetrapeptide" 1992 *Am. J. Physiol.*, 263:R125-R135.
Asin, "A-71623, a selective CCK-A receptor agonist, suppresses food intake in the mouse, dog, and monkey" Aug. 1992 *Pharmacol. Biochem. Behav.*, 42(4):699-704. PMID: 1513850.
Banfi, "Identification and characterization of the gene causing type 1 spinocerebellar ataxia" Aug. 1994 *Nature Genetics*, 7(4):513-520.
Bassuk, "A homozygous mutation in human PRICKLE1 causes an autosomal-recessive progressive myoclonus epilepsy-ataxia syndrome," Nov. 2008 *Amer. J. Hunt Genet.*, 83:572-581.
Bellissimo, "Cholecystokinin-A receptors are involved in food intake suppression in rats after intake of all fats and carbohydrates tested" Jan. 2003 *The Journal of Nutrition*, 133(7):2319-2325.
Berna, "Progress in developing cholecystokinin (CCK)/gastrin receptor ligands which have therapeutic potential" Dec. 2007 *Curr Opin Pharmacol.*, 7(6):583-592.
Berna, "Role of CCK/gastrin receptors in gastrointestinal/metabolic diseases and results of human studeis using gastrin/CCK receptor agonists/antagonists in these diseases" 2007 *Top Med Chem.*, 7(12):1211-1231.
Bhat, "Axon-glia interactions and the domain organization of myelinated axons requires neurexin IV/Caspr/Paranodin" May 2001 *Neuron*, 30(2):369-383.
Bignon, "SR146131: a new potent, orally active, and selective nonpeptide cholecystokinin subtype 1 receptor agonist. I. In vitro studies" May 1999 *J Pharmacol Exp Ther.*, 289(2):742-51.
Bignon, "SR146131: a new potent, orally active, and selective nonpeptide cholecystokinin subtype 1 receptor agonist. II. In vitro studies" May 1999 *J Pharmacol Exp Ther.*, 289(2):752-61.
Blankenberg, "Galaxy: a web-based genome analysis tool for experimentalists" Jan. 2010 *Current Protocols in Molecular Biology*, Chapter 19, Unit 19.10.1-21.
Bolger, "Trimmomatic: A flexible trimmer for Illumina Sequence Data" Aug. 2014 *Bioinformatics*, 30(15):2114-2120.
Bradwejn, "Cholecystokinin-tetrapeptide induces panic attacks in patients with panic disorder" Feb. 1990 *The Canadian Journal of Psychiatry /La Revue Canadienne de Psychiatrie*, 35(1):83-85.
Burright, "SCA1 transgenic mice: a model for neurodegeneration caused by an expanded CAG trinucleotide repeat" Sep. 1995 *Cel* 82:937-948.

(Continued)

*Primary Examiner* — Jeffrey S Lundgren
*Assistant Examiner* — Michael J Schmitt
(74) *Attorney, Agent, or Firm* — Mueting Raasch Group

(57) ABSTRACT

A method for treating a subject having, or at risk of having, ataxia, generally includes administering to the subject an amount of a composition comprising a cholecystokinin receptor (Cck1R) agonist effective to ameliorate at least one symptom or clinical sign of ataxia.

5 Claims, 15 Drawing Sheets
(12 of 15 Drawing Sheet(s) Filed in Color)
Specification includes a Sequence Listing.

(56) References Cited

OTHER PUBLICATIONS

Bushart, "Precision medicine in spinocerebellar ataxias: treatment based on common mechanisms of disease" 2016 *Annals of Translational Medicine*, 4(2). http://doi.org/10.3978/j.issn.2305-5839.2016.01.06.

Campos, "CCK-induced reduction of food intake and hindbrain MAPK signaling are mediated by NMDA receptor activation" Jun. 2012 *Endocrinology*, 153(6):2633-2646. Online: http://doi.org/10.1210/en.2012-1025.

Cannon, "Alternate drug delivery routes for A-71623, a potent cholecystokinin-a receptor agonist tetrapeptide" 1996 *J. Drug Targeting*, 4:69-78.

Carlson, "Emerging pathogenic pathways in the spinocerebellar ataxias" 2009 *Curr. Opin. Genet. Dev.*, 19:247-253.

Castillo, "Effect of oral CCK-1 agonist GI181771X on fasting and postprandial gastric functions in healthy volunteers" Aug. 2004 *Am J Physiol Gastrointest Liver Physiol.*, 287(2):G363-9.

Chen, "The Structure of the AXH Domain of Spinocerebellar Ataxin-1" Jan. 2004 *J. Biol. Chem.*, 279:3758-3765.

Chopra, Translating cerebellar Purkinje neuron physiology to progress in dominantly inherited ataxia 2014 *Future Neurology*, 9(2):187-196.

Chung, "Cholecystokinin excites interneurons in rat basolateral amygdala" 2009 Journal of *Neurophysiology*, 102(1):272-284. http://doi.org/10.1152/jn.90769.2008.

Chung, "Evidence for a mechanism predisposing to intergenerational CAG repeat instability in spinocerebellar ataxia type 1" Nov. 1993 *Nat Genet.*, 5:254-258.

Clark, "Purkinje cell expression of a mutant allele of SCA1 in transgenic mice leads to disparate effects on motor behaviors followed by a progressive cerebellar dysfunction and histological alterations" Oct. 1997 *J. Neurosci.*, 17:7385-7395.

Clark, "Spinocerebellar ataxia type 1—modeling the pathogenesis of a polyglutamine neurodegenerative disorder in transgenic mice" Apr. 2000 *Journal of Neuropathology and Experimental Neurology*, 59(4):265-270.

Cong, "Expression and cell-specific localization of cholecystokinin receptors in rat lung" 2003 *World Journal of Gastroenterology: WJG*, 9(6):1273-1277. http://doi.org/10.3748/wjg.v9.i6.1273.

Crespo-Barreto, "Partial loss of ataxin-1 function contributes to transcriptional dysregulation in spinocerebellar ataxia type 1 pathogenesis" 2010 *PLoS Genet.*, 6:e1001021.

Cvetanovic, "Early activation of microglia and astrocytes in mouse models of spinocerebellar ataxia type 1" Mar. 2015 *Neuroscience*, 289:289-299.

Dansithong, "Ataxin-2 regulates RGS8 translation in a new BAC-SCA2 transgenic muse model" 2015 *PLoS Genetics*, 11:e1005182.

De Chiara, "The AXH module: an independently folded domain common to ataxin-1 and HBP1" Sep. 2003 *FEBS Letter*, 551:107-112.

De Chiara, "Phosphorylation of S776 and 14-3-3 Binding Modulate Ataxin-1 Interaction with Splicing Factors" Dec. 2009 *PLoS One 4*, e8372.

Deng, "Cholecystokinin facilitates glutamate release by increasing the No. Of readily releasable vesicles and releasing probability" Apr. 2010 *The Journal of Neuroscience: The Official Journal of the Society for Neuroscience*, 30(15):5136-5148.

Deninno, "Development of CCK-tetrapeptide analogues as potent and selective CCK-A receptor agonists" 1990 *J.Med.Chem.*, 33:2951.

Dietl, "On the distribution of cholecystokinin receptor binding sites in the human brain: an autoradiographic study" 1987 *Synapse* (New York, N.Y.), 1(2):169-183.

Dockray, "Cholecystokinins in rat cerebral cortex: identification, purification and characterization by immunochemical methods" 1980 *Brain Research*, 188(1):155-165.

Doyle, "Application of a translational profiling approach for the comparative analysis of CNS cell types" Oct. 2008 *Cell*, 135:749-762.

Duarte-Neves, "Neuropeptide Y mitigates neuropathology and motor deficits in mouse models of Machado-Joseph disease" Oct. 2015 *Hum. Mol. Genet.* 24(19): 5451-5463.

Dufresne, "Molecular cloning, developmental expression and pharmacological characterization of the CCKB/gastrin receptor in the calf pancreas" 1996 *European Journal of Pharmacology*, 297(1-2): 165-179.

Dufresne, "Cholecystokinin and gastrin receptors" 2006 *Physiol. Rev.*, 86:805-847.

Duvick, "SCA1-like disease in mice expressing wild type ataxin-1 with a serine to aspartic acid replacement at residue" Sep. 2010 *Neuron*, 67(6):929-935.

Emamian, "Serine 776 of ataxin-1 is critical for polyglutamine-nduced disease in SCA1 transgenic mice" May 2003 *Neuron* 38(3):375-387.

Fogel, "Mutation of senataxin alters disease-specific transcriptional networks in patients with ataxia with oculomotor apraxia type 2" Sep. 2014 *Hum. Mol. Genet.*, 2(18):4758-4769.

Foskett, "Inositol trisphosphate receptor Ca2+ release channels in neurological diseases" Jul. 2010 *Pflügers Archiv: European Journal of Physiology*, 460(2):481-494. http://doi.org/10.1007/s00424-010-0826-0.

Fryer, "Exercise and genetic rescue of SCA1 via the transcriptional repressor Capicua" Nov. 2011 *Science*, 334(6056):690-693.

Fu, "Variation of the CGG repeat at the fragile X site results in genetic instability: Resolution of the Sherman paradox" Dec. 1991 *Cell*, 67(6):1047-1058.

García-López, "Strategies for design of non peptide CCK1R agonist/antagonist ligands" 2007 *Curr Top Med Chem.*, 7(12):1180-94.

Gehrking, "Partial Loss of Tip60 Slows Midstage Neurodegeneration in a Spinocerebellar Ataxia Type 1 (SCA1) Mouse Model" Jun. 2011 *Hum. Mol. Genet.*, 20(11):2204-2212.

Giardine, "Galaxy: a platform for interactive large-scale genome analysis" Sep. 2005 *Genome Research*, 15(10):1451-1455. http://doi.org/10.1101/gr.4086505.

Goebel-Stengel, "CCK-8 and CCK-58 differ in their effects on nocturnal solid meal pattern in undisturbed rats" Aug. 2012 *Am J Physiol Regul Integr Comp Physiol.*, 303(8), R850-860. doi:10.1152/ajpregu.00365.2011.

Goecks, "Web-based visual analysis for high-throughput genomics" 2013 *BMC Genomics*, 14:397. http://doi.org/10.1186/1471-2164-14-397.

Goff, "CummeRbund: Analysis, exploration, manipulation, and visualization of Cufflinks high-throughput sequencing data. R package version 2.8.2" May 7, 2014. Online: http://compbio.mit.edu/cummeRbund/.

Haines, "Spinocerebellar ataxia in a large kindred: age at onset, reproduction, and genetic likage studies" Dec. 1984 *Neurology*, 34:1542-1548.

Heiman, "Cell type-specific mRNA purification by translating ribosome affinity purification (TRAP)" Nov. 2014 *Nature Protocols*, 9(6):1282-1291.

Heldsinger, "Cocaine- and amphetamine-regulated transcript is the neurotransmitter regulating the action of cholecystokinin and leptin on short-term satiety in rats" Nov. 2012 *American Journal of Physiology. Gastrointestinal and Liver Physiology*, 303(9):G1042-1051.

Hodges, "Regional and cellular gene expression changes in human Huntington's disease brain" 2006 *Human Molecular Genetics*, 15(6):965-977.

Huttlin, "A tissue-specific atlas of mouse protein phosphorylation and expression" Dec. 2010 *Cell*, 143(7):1174-1189.

Iadarola, "Alterations in cholecystokinin peptide and mRNA in actively epileptic human temporal cortical foci" 1991 *Epilepsy Research*, 8(1):58-63.

Iadorola, "Changes in dynorphin, encephalin, and cholecystokinin content of hippocampus and substantia nigra after amygdala kindling" Feb. 1986 *Brain Research*, 365(1):185-191.

Ikeda, "Enhanced inhibitory neurotransmission in the cerebellar cortex of Atpla3-deficient heterozygous mice" Jul. 2013 *The Journal of Physiology*, 591(13), 3433-3449.

(56) References Cited

OTHER PUBLICATIONS

Ingram, "Cerebellar Transcriptome Profiles of ATXN1 Transgenic Mice Reveal SCA1 Disease Progression and Protection Pathways" Mar. 2016 Neuron, 89(6):1194-1207. doi: 10.1016/j.neuron.2016.02.011.

Jafar-Nejad, "Regional rescue of spinocerebellar ataxia type 1 phenotypes by 14-3-3E haploinsufficiencey in mice underscores complex pathogenicity in neurodegeneration" 2011 Prc. Natl. Acad. Scu USA, 108:2142-2147.

Jordan, "Stimulation of cholecystokinin-A receptors with G181771X does not cause weight loss in overweight or obese patients" Feb. 2008 Clin. Pharm. & Thera., 83:281-7.

Jorgensen, "Phosphorylation of ATXN1 at Ser776 in the Cerebellum" Jul. 2009 J. Neurochem. 110(2):675-686.

Kádár, "Multiple treatment potentiates the anticonvulsive activity of cholecystokinin octapeptides" Nov.-Dec. 1985 Peptides, 6(6):1009-1014.

Kádár, "Inhibition of seizures induced by picrotoxin and electroshock by cholecystokinin octapeptides and their fragments in rats after intracerebroventricular administration" 1984 Neuropharmacology, 23(8):955-961.

Kagami, "Investigation of differentially expressed genes during the development of mouse cerebellum" 2001 Brain Research. Gene Expression Patterns, 1(1):39-59.

Kawamura-Saito, "Fusion between CIC and DUX4 up-regulates PEA3 family genes in Ewing-like sarcomas with t(4;19)(q35;q13) translocation" Jul. 2006 Hum. Mol. Genet., 15(13):2125-2137.

Kim, "Structural basis of protein complex formation and reconfiguration by polyglutamine . disease protein Ataxin-1 and Capicua" Mar. 2013 Genes Dev., 27(6):590-595.

Kim, "TopHat2: accurate alignment of transcriptomes in the presence of insertions, deletions and gene fusions" 2013 Genome Biology, 14(R36):1-13.

Klement, "Ataxin-1 nuclear localization and aggregation: Role in polyglutamine-induced disease in SCA1 transgenic mice" Oct. 1998 Cell, 95:41-53.

Klockgether, "Update on degenemative ataxias" Aug. 2011 Curr. Opin. Neurol., 24(4):339-345.

Koeppen, "The pathogenesis of spinocerebellar ataxia" 2005 Cerebellum 4(1):62-73.

Koeppen, "The hereditary ataxias" Jun. 1998 J Neuropathol. Exp. Neurol. 57:531-543.

Kopin, "The cholecystokinin-A receptor mediates inhibition of food intake yet is not essential for the maintenance of body weight" Feb. 1999 Journal of Clinical Investigation, 103(3):383-391.

Lacourse, "Pancreatic function in CCK-deficient mice: adaptation to dietary protein does not require CCK" 1999 The American Journal of Physiology, 276(5 Pt 1):G1302-1309.

Lam, "Mutant ATAXIN-1 interacts with the repressor Capicua in its native complex to cause SCA1 neuropathology" Dec. 2006 Cell, 127(7):1335-1347.

Langfelder "WGCNA: an R package for weighted correlation network analysis" Dec. 2008 BMC Bioinformatics, 9:559.

Langfelder, "When is hub gene selection better than standard meta-analysis?" Apr. 2013 PLoS One, 8(4):e61505.

Langhans, "Abnormal Gastric Histology and Decreased Acid Production in Cholecystokinin-13/Gastrin Receptor-Deficient Mice" 1997 Gastroenterology, 112:280-286.

Langmead, "Aligning short sequencing reads with Bowtie" 2010 Current Protocols in Bioinformatics / Editoral Board, Andreas D. Baxevanis . . . [et Al.], Cover page, title page, table of contents and Chapter 11, Unit 11.7.

Laspada, "Trinucleotide repeat expansion in neurological disease" 1994 Annals of Neurology, 36(6), 814-822.

Lassman, "Defining the role of cholecystokinin the lipid-induced human brain activation matrix" Apr. 2010 Gastroenterology, 138(4), 1514-1524.

Lay, "Murine prenatal expression of cholecystokinin in neural crest, enteric neurons, and enteroendocrine cells" Oct. 1999 Develop. Dynamics, 216(2):190-200.

Lee, "Cholecystokinin: a multi-functional molecular switch of neuronal circuits" Jan. 2011 Dev. Neurobiol. 71(1): 83-91.

Lein, "Genome-wide atlas of gene expression in the adult mouse brain" Dec. 2006 Nature, 445(7124), 168-176.

Len, "Genome-wide atlas of gene expression in the adult mouse brain" Jan. 2007 Nature 445:168-176.

Lidwell, "Possible role for the FosB/JunD AP-1 transcription factor complex in glutamate-mediated excitotoxicity in cultured cerebellar granule cells" Nov. 2000 J. Neurosci. Res. 62(3):427-439.

Lim, "Opposing effects of polyglutamine expansion on native protein complexes contribute to SCA1" Apr. 2008 Nature, 452(7188):713-719.

Lin, "Polyglutamine expansion downregulates specific neuronal genes before pathologic changes in SCA1" Feb. 2000 Nat. Neurosci., 3(2):157-163.

Lin, "Characterization of two novel cholecystokinin tetrapeptide (30-33) analogues, A-71623 and A-70874, that exhibit high potency and selectivity for cholecystokinin-A receptors" Aug. 1990 Mol. Pharmacol., 39(3):346.

Lin, "A71378: a CCK agonist with high potency and selectivity for CCK-A receptors" 1990 The American Journal of Physiology, 258(4 Pt 1), G648-651.

Little, "Mapping glucose-mediated gut-to-brain signalling pathways in humans" Aug. 2014 Neuroimage, 96(100), 1-11.

Liu, "Deranged calcium signaling and neurodegeneration in spinocerebellar ataxia type 2" 2009 The Journal of Neuroscience: The Official Journal of the Society for Neuroscience, 29(29), 9148-9162.

Liu, "Prickel1 is expressed in distinct cell populations of the central nervous system and contributes to neuronal morphogenesis" Jun. 2013 Hum. Mol. Genet., 22(11):2234-2246.

Lo, "Characterization of mice lacking the gene for cholecystokinin. American Journal of Physiology" 2008 Regulatory, Integrative and Comparative Physiology, 294(3), R803-810. http://doi.org/10.1152/ajpregu.00682.2007.

Lo, "Intraperitoneal CCK and fourth-intraventricular Apo AIV require both peripheral and NTS CCK1R to reduce food intake in male rats" 2014 Endocrinology, 155(5), 1700-1707. Online: http://doi.org/10.1210/en.2013-1846.

Luyer, "Nutritional stimulation of cholecystokinin receptors inhibits inflammation via the vagus nerve" Oct. 2005 The Journal of Experimental Medicine, 202(8), 1023-1029. http://doi.org/10.1084/jem.20042397.

Machanick, "MEME-ChIP motif analysis of large DNA datasets" Jun. 2011 Bioinfomatics, 27(12):1696-1697.

Manni, "Effects of Cholecystokinin-8 in Peripheral Neuropathies: A Nerve Growth Factor Mediated Action?" 2003 Archives Italiennes de Biologie, 141:117-126.

Matilla, "Mice lacking Ataxin-1 display teaming deficits and decreased hippocampal paired-pulse facilitation" Jul. 1998 J. Neurosic., 18(14):5508-5516.

Matsui, "Levels of somatostatin and cholecystokinin in the brain of ataxic mutant mice" 1993 Life Sciences, 53(4):333-340.

Meis, "Postsynaptic mechanisms underlying responsiveness of amygdaloid neurons to cholecystokinin are mediated by a transient receptor potential-like current" 2007 Molecular and Cellular Neurosciences, 35(2):356-367.

Miaymoto, "Cholecystokinin Plays a Novel Protective Role in Diabetic Kidney through Anti-inflammatory Actions on a Macrophage" Apr. 2012 Diabetes, 61.

Oberdick, "A promoter that drives transgene expression in cerebellar Purkinje and retinal bipolar neurons" Apr. 1990 Science, 248(4952):223-226.

Oldham, "Functional organization of the transcriptome in human brain" Nov. 2008 Nat. Neurosci., 11(11):1271-1282.

Opal, "Spinocerebellar Ataxia Type 1 Synonym: SCA1" Oct. 1998 Gene Reviews, 1-56.

Orr, "Expansion of an unstable trinucleotide CAG repeat in spinocerebellar ataxia type 1" Jul. 1993 Nat. Genet., 4(3):221-226.

Orr, "The ins and outs of a polyglutamine neurodegenerative disease: spinocerebellar ataxia type 1 (SCA1)" Jun. 2000 Neurobiol. Dis., 7:129-134.

(56) References Cited

OTHER PUBLICATIONS

Orr, "SCA1 Pathogenesis: Genetic Dissection of a Neurodegenerative Disease" Yale Department of Genetics Seminar Presentation, New Haven, CT, Feb. 2, 2016.
Oz, "Neurochemical alterations in spinocerebellar ataxia type 1 and their correlations with clinical status" Jul. 2010 *Movement Disorders: Official Journal of the Movement Disorder Society*, 25(9):1253-1261. http://doi.org/10.1002/mds.23067.
Parikshak, "Systems biology and gene networks in neurodevelopmental and neurodegenerative disorders" Aug. 2015 *Nat. Rev. Genet.*, 16(8):441-458.
Park, "RAS-MAPK-MSK1 pathway modulates ataxin 1 protein levels and toxicity in SCA1" 2013 *Nature*, 498(7454), 325-331. http://doi.org/10.1038/nature12204.
Pratt, "Cleavage-Site Mutagenesis Alters Post-translation Processing of Pro-CCK in AtT-20 Cells" 2014 *Biochemistry*, 43:9502-9511.
Presson, "Integrated weighted gene co-expression network analysis with an application to chronic fatigue syndrome" Nov. 2008 *BMC Syst Biol.*, 2(95).
Prudencio, "Distinct brain transcriptome profiles in C9orf72-associated and sporadic ALS" Aug. 2015 *Nat. Neurosci.*, 18(8):1175-1182.
Reeve, "Differences in receptor binding and stability to enzymatic digestion between CCK-8 and CCK-58" Oct. 2002 *Pancreas*, 25(3):e50-55.
Rehfeld, "On the tissue-specific processing of procholecystokinin in the brain and gut—a short review" 2003 *Journal of Physiology and Pharmacology: An Official Journal of the Polish Physiological Society*, 54 Suppl 4:73-79.
Reidelberger, "Effects of peripheral CCK receptor blockade on food intake in rats" Aug. 2003 *American Journal of Physiology. Regulatory, Integrative and Comparative Physiology*, 285(2):R429-437. Online: http://doi.org/10.1152/ajpregu.00176.2003.
Rindi, "Abnormal gastric morphology and function in CCK-B/gastrin receptor-deficient mice" May-Aug. 1998 *The Yale Journal of Biology and Medicine*, 71(3-4):347-354.
Roberts, "Improving RNA-Seq expression estimates by correcting for fragment bias" Mar. 2011 *Genome Biology*, 12(R22):1-14.
Rogers, "Mechanisms of action of CCK to activate central vagal afferent terminals" 2008 *Peptides*, 29(10):1716-1725.
Rong, "Identification of candidate Purkinje cell-specific markers by gene expression profiling in wild-type and pcd$^{2J}$ mice" Dec. 2004 *Mol. Brain Res.*, 132(2):128-145.
Ruegsegger, "Impaired mTORC1-dependent expression of Homer-3 influences SCA1 pathophysiology" Jan. 2016 *Neuron* 89(1):129-146.
Rünkorg, "Differences in behavioural effects of amphetamine and dopamine-related gene expression in wild-type and homozygous CCK2 receptor deficient mice" 2006 *Neuroscience Letters*, 406(1-2):17-22.
Sato, "Cerebellar development transcriptome database (CDT-DB): profiling of spatio-temporal gene expression during the postnatal development of mouse cerebellum" Oct. 2008 *Neural Networks: The Official Journal of the International Neural Network Society*, 21(8):1056-1069.
Schmassmann, "Cholecystokinin type B receptor antagonist PD-136,450 is a partial secretory agonist in the stomach and a full agonist in the pancreas of the rat" Feb. 1994 *Gut*, 35:270-274.
Schmitz, "Identification of cholecystokinin-B/gastrin receptor domains that confer high gastrin affinity: utilization of a novel Xenopus laevis cholecystokinin receptor" Aug. 1996 *Molecular Pharmacology*, 50(2):436-441.
Schorge, "Human ataxias: a genetic dissection of inositol triphosphate receptor (ITPR1)-dependent signaling" May 2010 *Trends Neurosci.*, 33(5):211-219.
Schut, "Hereditary ataxia: Clinical study through six generations" Jun. 1951 *Arch. Neurol. Psychiatry*, 63:535-568.
Sekiguchi, "A comparative study on characterization and distribution of cholecystokinin binding sites among the rat, mouse and guinea pig brain" Dec. 1986 *Brain Research*, 399(2):271-281.

Serra, "Gene profiling links SCA1 pathophysiology to glutamate signaling in Purkinje cells of transgenic mice" Oct. 2004 *Hum. Mol. Genet.*, 13(20):2535-2543.
Serra, "RORa-mediated Purkinje cell development determines disease severity in adult SCA1 mice" Nov. 2006 *Cell*, 127(4):697-708.
Shinzawa, "Neuroaxonal dystrophy caused by group VIA phospholipase A2 deficiency in mice: a model of human neurodegenerative disease" Feb. 2008 *The Journal of Neuroscience: The Official Journal of the Society for Neuroscience*, 28(9):2212-2220. Online: http://doi.org/10.1523/JNEUROSCI.4354-07.2008.
Simmons, "ARL 15849: A Selective CCK-A Agonist with Anorectic Activity in the Rat and Dog" Feb. 1998 *Pharmacology Biochemistry and Behavior*, 59(2):439-444.
Smeyne, "Dynamic organization of developing Purkinje cells revealed by transgene expression" Nov. 1991 *Science* (New York, N.Y.), 254(5032):719-721.
Solomon, "Bioactivity of cholecystokinin analogues: CCK-8 is not more potent than CCK-33" Jul. 1984 *American Journal of Physiology—Gastrointestinal and Liver Physiology*, 247(1):G105-G111.
Stark, "CCK-JMV-180: a peptide that distinguishes high-affinity cholecystokinin receptors from low-affinity cholecystokinin receptors" Feb. 1989 *Biochimica et Biophysica Acta (BBA)—Molecular Cell Research*, 1010(2): 145-150.
Subramony, "Spinocerebellar Ataxia Type 1. Synonym: SCA1" Update Jul. 3, 2014. *Gene Reviews*, 19 pages.
Sugaya, "Cholecystokinin Protects Cholinergic Neurons against Basal Forebrain Lesion" 1992 *Japan Journal of Pharmacology*, 59:125-128.
Sui, "Female mice lacking cholecystokinin 1 receptors have compromised neurogenesis, and fewer dopaminergic cells in the olfactory bulb" 2013 *Frontiers in Cellular Neuroscience*, 7.
Sun, "Spinocerebellar ataxia: relationship between phenotype and genotype—A Review" Oct. 2016 *Clinical Genetics*, n/a-n/a.
Sutton, "Extracellular Signal-Regulated Kinase 1/2 Signaling Pathway in Solitary Nucleus Mediates Cholecystokinin-Induced Suppression of Food Intake in Rats" 2004 *The Journal of Neuroscience*, 24(45):10240-10247. Online: http://doi.org/10.1523/JNEUROSCI.2764-04.2004.
Tagen, "Recombinant prohormone convertase 1 and 2 cleave purified pro cholecystokinin (CCK) and a synthetic peptide containing CCK 8 Gly Arg Arg and the carboxyl-terminal flanking peptide" Dec. 2005 *Peptides*, 26(12):2530-2535.
Tamura, "Mechanisms of cholecystokinin-induced protection of cultured cortical neurons against N-methyl-d-aspartate receptor-mediated glutamate cytotoxicity" 1992 *Brain Research*, 592(1-2), 317-325.
Tirassa, "Colecystokinin-8 protects central cholinergic neurons against fimbria-fornix lesion through the up-regulation of nerve growth factor synthesis" 1999 *Proc. Natl. Acad. Sci.* 96:6473-6477.
Tirassa, "Cholecystokinin-8 regulation of NGF concentrations in adult mouse brain through a mechanism involving CCKA and CCKB receptors" 1998 *British Journal of Pharmacology*, 123 (6): 1230-1236. http://doi.org/10.1038/sj.bjp.0701718.
Tissir, "Shaping the nervous system: role of the core planar cell polarity genes" Aug. 2013 *Nat. Rev. Neurosci.*, 14(8):525-535.
Tocris, "A-71623: Certificate of Analysis" Nov. 1, 2016, 2 pages.
Trapnell, "Transcript assembly and quantification by RNA-Seq reveals unannotated transcripts and isoform switching during cell differentiation" May 2010 *Nat. Biotechnol.*, 28(5):511-515.
Trapnell, "Differential gene and transcript expression analysis of RNA-seq experiments with TopHat and Cufflinks" Mar. 2012 *Nat Protoc.*, 7(3):562-578.
Trapnell, "TopHat: discovering splice junctions with RNA-Seq." 2009 *Bioinformatics* (Oxford, England), 25(9):1105-1111. Online: http://doi.org/10.1093/bioinformatics/btp120.
Tsai, "Ataxin 1, a SCA1 neurodegenerative disorder protein, is functionally linked to the silencing mediator of retinoid and thyroid hormone receptors" Mar. 2004 *Proc. Natl. Acad. Sci. U. S. A.*, 101(12):4047-4052.
Tsuda, "The AXH domain in mammalian/Drosophila Ataxin-1 mediates neurodegeneration in spinocerebellar ataxia 1 through its interaction with Gfi-1/Senseless proteins" Aug. 2005 *Cell*, 122(4):633-644.

(56) References Cited

OTHER PUBLICATIONS

Uhlén, "Proteomics. Tissue-based map of the human proteome" 2015 *Science* (New York, N.Y.), 347(6220): 1260419.

Vandaele, "Purkinje-cell-protein-2 regulatory regions and transgene expression in cerebellar compartments" Jul. 1991 *Genes Develop.*, 5(7):1136-1148.

Verge, "Differential influence of nerve growth factor on neuropeptide expression in vivo: a novel role in peptide suppression in adult sensory neurons" Mar. 1995 *Journal of Neuroscience*, 15, 2081-2096.

Verge, "Cholecystokinin in mammalian primary sensory neurons and spinal cord: in situ hybridization studies on rat and monkey spinal ganglia" 2013 *European Journal of Neuroscience*, 5:240-250.

Wang, "Discovery of pyrimidine carboxamides as potent and selective CCK1 receptor agonists" May 2011 *Bioor. Med. Chem. Letts.*, 21(10):2911-2915.

Wang, "Effect of gallbladder hypomotility on cholesterol crystallization and growth in CCK-deficient mice" 2010 *Biochimica Et Biophysica Acta*, 1801(2):138-146.

Wang, "Cholecystokinin facilitates neuronal excitability in the entorhinal cortex via activation of TRPC-like channels" 2011 *Journal of Neurophysiology*, 106(3):1515-1524. http://doi.org/10.1152/jn.00025.2011.

Williams, "Polyglutamine Neurodegeneration: Protein Misfolding Revisited" 2008 *Trends in Neurosciences*, 31(10), 521-528.

Wilson, "Concurrent chronic administration of a CCK(B) antagonist can decrease tolerance to the ataxic effects of ethanol" Jan. 1999 *Addict Biol.*, 4(1):35-45.

Wyeth, "Increased cholecystokinin labeling in the hippocampus of a mouse model of epilepsy maps to spines and glutamatergic terminals" Jan. 2012 *Neuroscience* 202:371-383. Online: http://www.ncbi.nlm.nih.gov/pubmed/22155653.

Xu, "Modular Genetic Control of Sexually Dimorphic Behaviors" 2012 *Cell*, 148(3):596-607. http://doi.org/10.1016/j.cell.2011.12.018.

Yamashita, "Neuropeptide-immunoreactive cells and fibers in the developing primate cerebellum Brain Research" 1990 *Developmental Brain Research*, 51(1): 19-25.

Yue, "The spinocerebellar ataxia type 1 protein, ataxin-1, has RNA-binding activity that is inversely affected by the length of its polyglutamine tract" 2001 *Hum. Mol. Genet.*, 10:25-30.

Zetler, "Anticonvulsant effects of careulein and cholecystokinin octapeptide, compared with those of diazepam" 1980 *European Journal of Pharmacology*, 65(2-3):297-300.

Zhang, "Decreased immunoreactive (IR) calcitonin gene-related peptide correlates with sprouting of IR-peptidergic and serotonergic neuronal processes in spinal cord and brain from the Wobbler mouse during motoneuron disease" 1992 *Brain Research*, 587(1):169-177.

Zhang, "A general framework for weighted gene co-expression network analysis" 2005 *Stat. Appl. Genet Mol. Biol.*, 4:Article 17, 1-37.

Zhang, "Cholecystokinin octapeptide regulates lipopolysaccharide-activated B cells co-stimulatory molecule expression and cytokines production in vitro" 2011 *Immunopharmacology and Immunotoxicology*, 33(1):157-163.

Zhu, "The cerebellum in feeding control: possible function and mechanism" 2008 *Cellular and Molecular Neurobiology*, 28(4):469-478.

Zoghbi, "Glutamine Repeats and Neurodegeneration" 2000 *Annual Review of Neuroscience*, 23(1):217-247. Online: http://doi.org/10.1146/annurev.neuro.23.1.217.

Zohgbi, "Spinocerebellar ataxia type 1" 1995 *Semin. Cell. Biol.* 6:29-35.

Zu, "Recovery from polyglutamine-induced neurodegeneration in conditional SCA1 transgenic mice" 2004 *The Journal of Neuroscience: The Official Journal of the Society for Neuroscience*, 24(40), 8853-8861. Online: http://doi.org/10.1523/JNEUROSCI.2978-04.2004.

* cited by examiner

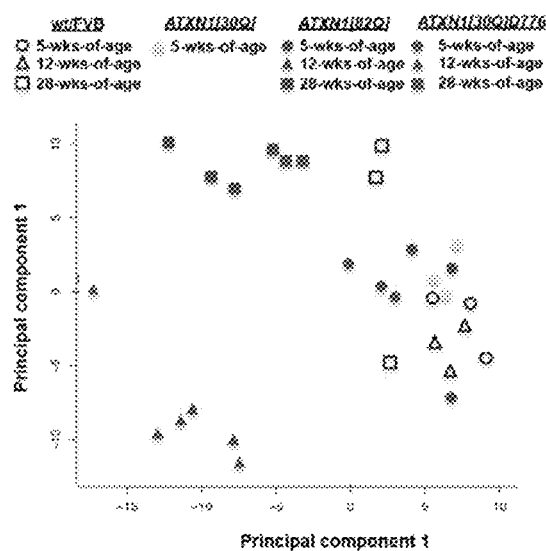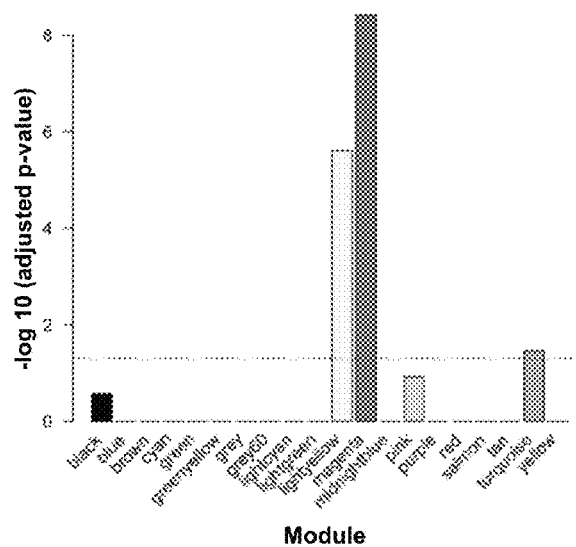
FIG. 1

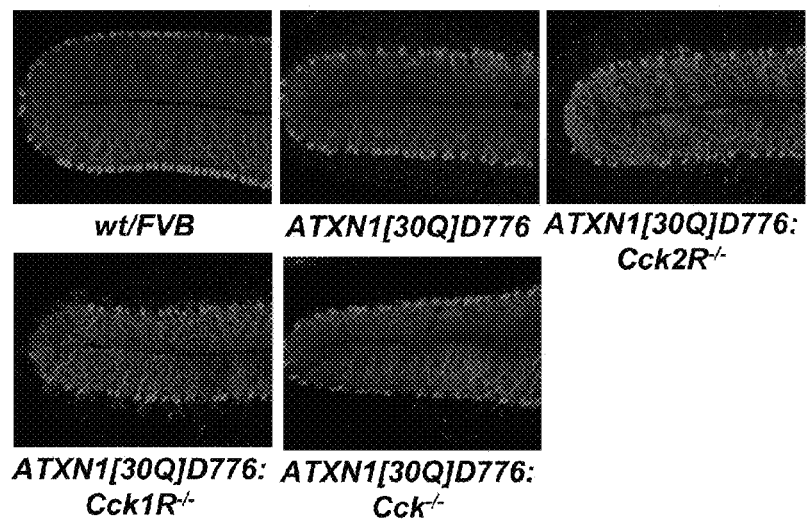
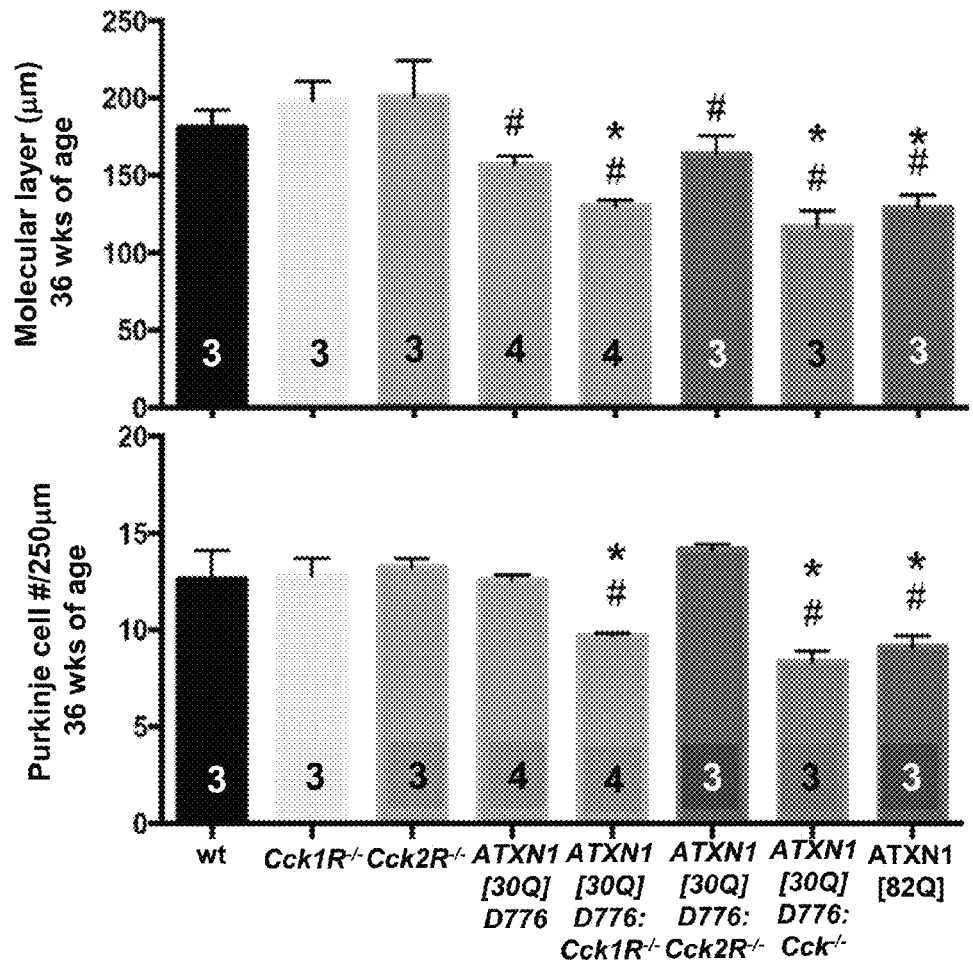
FIG. 6

A
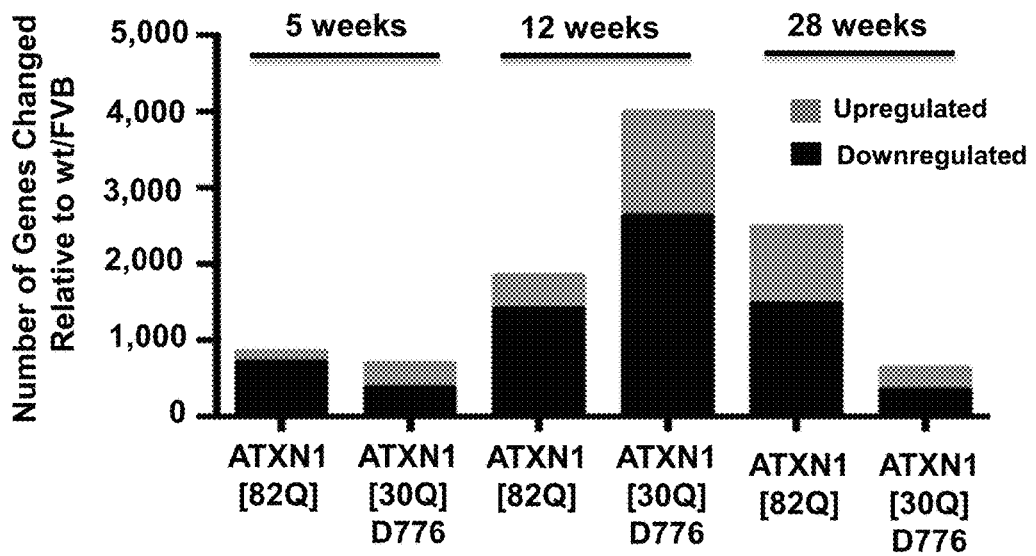
B
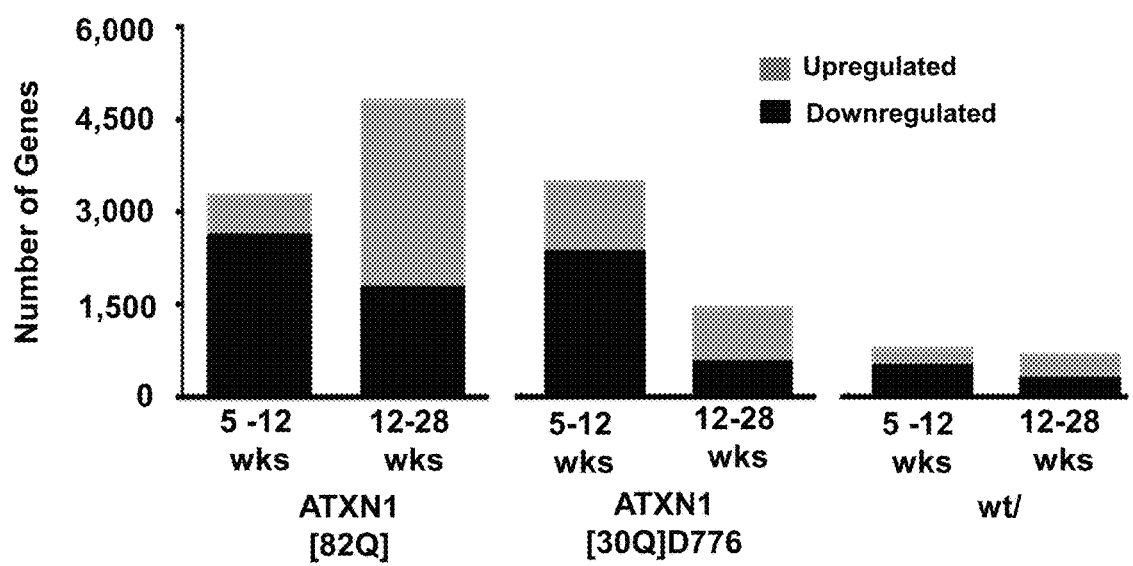
FIG. 7

Magenta Module

| PC-exclusive, strong (117) | PC-exclusive, weak (58) | PC-enriched (15) | Multiple Cell Types (31) |
|---|---|---|---|
| 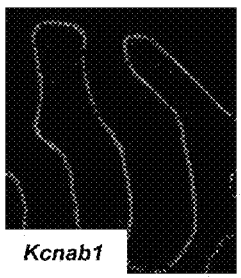 | 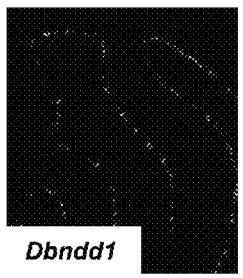 |  |  |
| *Kcnab1* | *Dbndd1* | *Gria3* | *Trp53bp2* |

| PC-exclusive, strong (117) | | | PC-exclusive, weak (58) | | PC-enriched (15) | Multiple Cell Types (31) |
|---|---|---|---|---|---|---|
| 1700018L02Rik | Ipo5 | Slc9a3 | Aldh7a1 | Tmem41a | Casp3 | Ccnd1 |
| 2310003H01Rik | Itpka | Spag5 | Ankrd33b | Tmtc1 | Casq2 | Ccni |
| 6030419C18Rik | Itpr1 | Spns2 | Arhgef2 | Trmt61a | Cdk16 | Dand5 |
| Ak129341 | Kalrn | Stk17b | Bean1 | Ttll3 | Cttnbp2 | Eif2ak3 |
| Ablim2 | Kcna6 | Susd4 | Capn2 | Vgll4 | Dgkz | Ephb2 |
| Agfg2 | Kcng4 | Taok3 | Ccdc64 | Vopp1 | Gabbr1 | Fbxl22 |
| Aldoc | Kcnip1 | Tex261 | Cdh1 | Wee1 | Gja1 | Gjb2 |
| Anks1b | Kctd12 | Tm6sf1 | Cep104 | Zfp346 | Gprc5b | Grm8 |
| Ano6 | Lhpp | Tnc | Cep72 | Zfp512 | Hs6st1 | Igfbp5 |
| Arap1 | Lhx5 | Trim9 | Cmtm3 | | Kif5a | Lynx1 |
| Atp2a3 | Mdfi | Trpc3 | Cnnm4 | | Lancl1 | Mxi1 |
| B3gnt2 | Mtss1 | Tspan11 | Cox6b2 | | Mthfsd | Nab2 |
| Baiap2 | Nlgn2 | Ttll5 | Cthrc1 | | Nr2f2 | Neurod2 |
| Bcar1 | Nup93 | Ubash3b | Dap | | Shank2 | Nkain1 |
| Bcl11a | Opn3 | Vimp | Dyrk3 | | | Nkd1 |
| Cacna1g | Orai2 | Wiz | Eif2ak1 | | | Padi2 |
| Cacnb2 | Pcp4 | Wsb2 | Elfn2 | | | Phactr3 |
| Calb1 | Pcsk6 | Ywhah | Etv4 | | | Rasal1 |
| Ccdc120 | Pde5a | Zdhhc14 | Exosc1 | | | Rgm |
| Cep76 | Pex26 | Zfp385c | Fgf7 | | | Rian |
| Cerk | Plcb3 | | Hk2 | | | Scn1b |
| Chst8 | Plekhd1 | | Hrh3 | | | St3gal5 |
| Clmn | Plxdc | | Imp4 | | | Stap2 |
| Cntnap5b | Polr3k | | Itgb1bp1 | | | Syt13 |
| Cpe1 | Ppapdc2 | | Kcnmb4 | | | Tbpl1 |
| Crg1 | Ppp1r16b | | Lrrfip1 | | | Tmod1 |
| Ctth3 | Ppp1r17 | | Mfsd12 | | | Tob1 |
| Dagla | Ppp4r4 | | Mrps25 | | | Tshz1 |
| Dbndd1 | Prkcg | | Nek2 | | | Utp23 |
| Dlg2 | Prmt8 | | Npr1 | | | Ypel4 |
| Dner | Psd2 | | Ociad2 | | | |
| Doc2b | Rdh11 | | Pcdhgb5 | | | |
| Fam107b | Reep2 | | Pkp3 | | | |
| Fam117a | Rgs8 | | Ppm1j | | | |
| Fam21 | Rhobtb2 | | Ptprm | | | |
| Far2 | Rnf145 | | Rab43 | | | |
| Fgd3 | Rnf19b | | Rbm19 | | | |
| Garnl3 | Ryr1 | | Rhod | | | |
| Gng13 | Samd8 | | Rnf157 | | | |
| Gria3 | Sbk1 | | Rps6kc1 | | | |
| Grid2 | Sec61a1 | | Rpusd3 | | | |
| Grid2ip | Sema7a | | Sept5 | | | |
| Grik1 | Shisa6 | | Slc35c1 | | | |
| Homer3 | Slc1a6 | | Slc39a6 | | | |
| Hpca | Slc20a1 | | Soat1 | | | |
| Hpcal1 | Slc41a3 | | Sppl2b | | | |
| Icmt | Slc5a1 | | Stac | | | |
| Id2 | Slc6a6 | | Synj2 | | | |
| Inpp4a | | | | | | |
| Inpp5a | | | | | | |

FIG. 8

A
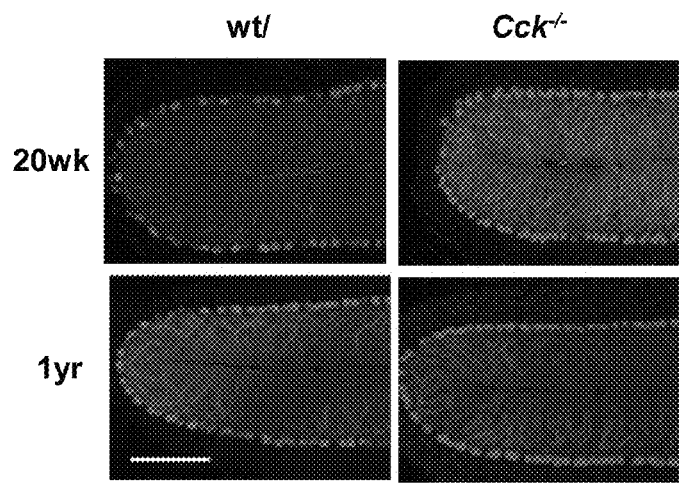
B
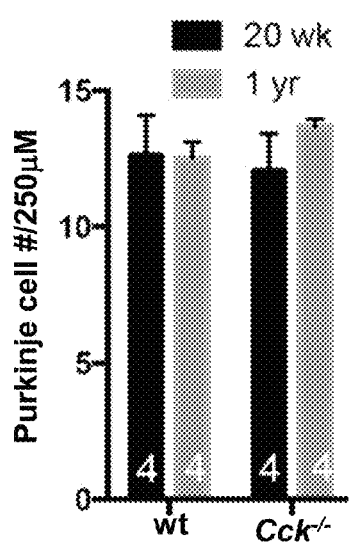
C
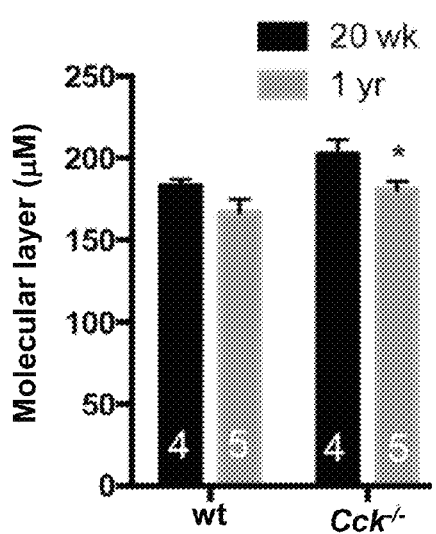
D
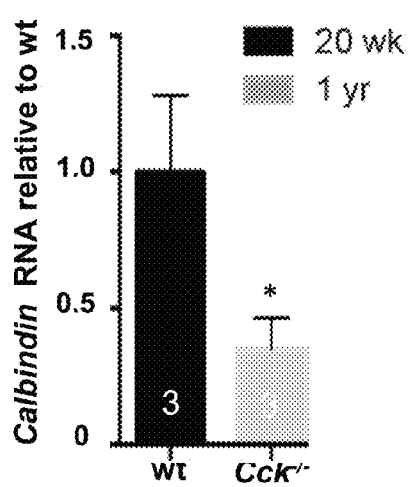
FIG. 11

SEQUENCE LISTING

```
<160> NUMBER OF SEQ ID NOS: 4

<210> SEQ ID NO 1
<211> LENGTH: 8
<212> TYPE: DNA
<213> ORGANISM: artificial
<220> FEATURE:
<223> OTHER INFORMATION: Cic binding motif

<400> SEQUENCE: 1 tgaatgaa                                                                  8

<210> SEQ ID NO 2
<211> LENGTH: 8
<212> TYPE: DNA
<213> ORGANISM: artificial
<220> FEATURE:
<223> OTHER INFORMATION: Cic binding motif

<400> SEQUENCE: 2 tgaatgga                                                                  8

<210> SEQ ID NO 3
<211> LENGTH: 90
<212> TYPE: DNA
<213> ORGANISM: artificial
<220> FEATURE:
<223> OTHER INFORMATION: Interrupted CAG repeat

<400> SEQUENCE: 3
cagcagcagc agcagcagca gcagcagcag cagcagcatc agcatcagca gcagcagcag         60
cagcagcagc agcagcagca gcagcagcag                                          90

<210> SEQ ID NO 4
<211> LENGTH: 246
<212> TYPE: DNA
<213> ORGANISM: artificial
<220> FEATURE:
<223> OTHER INFORMATION: CAG repeat

<400> SEQUENCE: 4
cagcagcagc agcagcagca gcagcagcag cagcagcagc agcagcagca gcagcagcag         60
cagcagcagc agcagcagca gcagcagcag cagcagcagc agcagcagca gcagcagcag        120
cagcagcagc agcagcagca gcagcagcag cagcagcagc agcagcagca gcagcagcag        180
cagcagcagc agcagcagca gcagcagcag cagcagcagc agcagcagca gcagcagcag        240
cagcag                                                                  246
```

ATAXIA THERAPEUTIC COMPOSITIONS AND METHODS

CROSS-REFERENCE TO RELATED APPLICATION

This application claims priority to U.S. Provisional Patent Application No. 62/303,122, filed Mar. 3, 2016, which is incorporated herein by reference.

GOVERNMENT FUNDING

This invention was made with government support under NS022920, NS045667, and NS027699, awarded by the National Institutes of Health. The government has certain rights in the invention.

SEQUENCE LISTING

This application contains a Sequence Listing electronically submitted to the United States Patent and Trademark Office via EFS-Web as an ASCII text file entitled "11005360101_SequenceListing_ST25.txt" having a size of 4 kilobytes and created on Mar. 3, 2017. The information contained in the Sequence Listing is incorporated by reference herein.

SUMMARY

This disclosure describes compositions and methods involved in treating ataxia. Generally, the compositions include an amount of a cholecystokinin receptor (Cck1R) agonist effective to ameliorate at least one symptom or clinical sign of ataxia. Generally, the methods include administering to a subject having, or at risk of having, ataxia an amount of the composition effective to ameliorate at least one symptom or clinical sign of ataxia.

In some embodiments, the method may be performed after the subject exhibits at least one symptom or clinical sign of ataxia. In other embodiments, the method may be performed before the subject exhibits at least one symptom or clinical sign of ataxia.

In some embodiments, the Cck1R is A71623. In some of these embodiments, the A71623 is administered to the subject to provide a dose of at least 20 µg/kg/day. In some of these embodiments, the A71623 is administered to the subject to provide a dose of A71623 1 mg/kg/day.

In some embodiments, the Cck1R is rebamipide.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing or photograph executed in color. Copies of this patent or patent application publication with color drawing(s) or photographs(s) will be provided by the Office upon request and payment of the necessary fee.

FIG. 1. Network analysis of ATXN1 mouse cerebellar gene expression. (A) Principal component analysis of ATXN1 transgenic mouse cerebellar RNA-seq data. (B) Correlation with disease for weighted gene co-expression analysis (WGCNA) Modules. Colors of bars correspond to WGCNA Module. Dashed line depicts statistical significance.

FIG. 6. Cck1R is required for protection against progressive Purkinje cell atrophy and death in ATXN1[30Q]D776 mice. (A) Representative images depicting primary cerebellar fissure showing Purkinje Cell morphology revealed by calbindin immunostaining. (B) Cerebellar molecular layer thickness for examined genotypes at 36 weeks of age. (C)

Purkinje Cell counts for examined genotypes at 36 weeks of age. Calbindin-positive Purkinje Cell bodies were counted within the primary fissure per 250 μm. Data in (B) and (C) mean, ±SEM. Two-Way ANOVA, Tukey post-hoc test. # indicates p<0.002 compared to wt. *p<0.01 compared to ATXN1[30Q]D776.

FIG. 7. Overview of cerebellar gene expression changes in ATXN1 transgenic mice. (A) Differentially expressed genes is cerebellar RNA from ATXN1[82Q] ATXN1[30Q] D776 mice at 5 weeks, 12 weeks, and 28 weeks. (B) Differentially expressed genes in cerebellar RNA between 5-12 weeks and 12-28 weeks within each genotype; ATXN1 [82Q], ATXN1[30Q]D776, and wt (FVB/NJ).

FIG. 8. Magenta module genes in situ hybridization (ISH) summary. Magenta Module genes are listed according to their ISH expression pattern as found on the Allen Brain Atlas (http://www.brain-map.org/). Sample ISH expression images for Purkinje Cell-exclusive strong, Purkinje Cell-exclusive weak, Purkinje Cell-enriched, and multiple cell types are presented with the list of Magenta genes with each expression pattern listed below.

Figure 9:
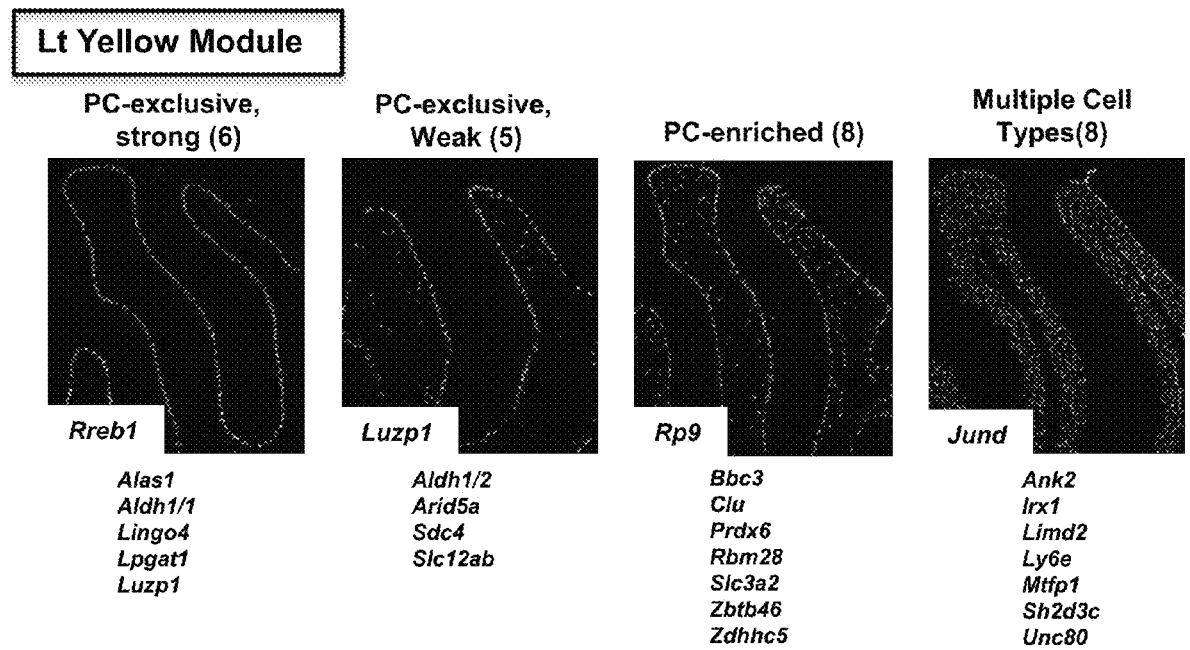

FIG. 9. Lt Yellow module genes ISH summary. Lt Yellow Module genes are listed according to their ISH expression pattern as found on the Allen Brain Atlas (http://www.brain-map.org/). Sample ISH expression images for Purkinje Cell-exclusive strong, Purkinje Cell-exclusive weak, Purkinje Cell-enriched, and multiple cell types are presented with the list of Lt Yellow genes with each expression pattern listed below.

Figure 10:
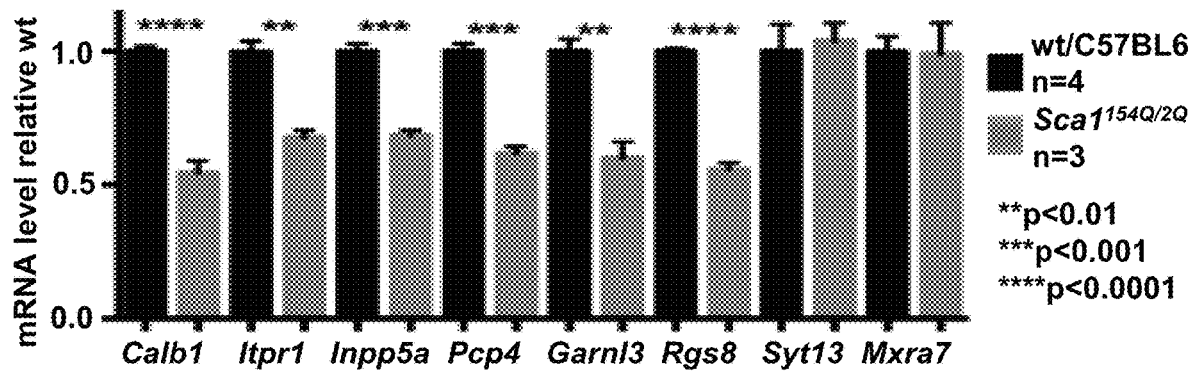

FIG. 10. qPCR analysis of a subset of Magenta Module genes in 12-week-old Atxn12Q/154Q cerebella.

FIG. 11. Cck−/− mice have altered cerebellar phenotypes but lack progressive cerebellar pathology. (A) Representative images depicting primary cerebellar fissure showing Purkinje cell morphology revealed by calbindin immunostaining. Scale bar, 200 μM applies to all images in this panel. (B) Purkinje cell counts for per 250 μM at 20 weeks and 1 year of age in wt and Cck−/− mice. (C) Changes in cerebellar molecular layer thickness at 20 weeks and 1 year of age in wt and Cck−/− mice. Data are represented as mean, ±SEM. Two-Way ANOVA, Tukey post-hoc test. *p<0.05. (D) qRT-PCR analysis of calbindin (Calb) mRNA levels in 1 year old in wt and Cck−/− mice. Data are represented as mean, ±SEM. Student's t-test. *p<0.05.

Figure 12:
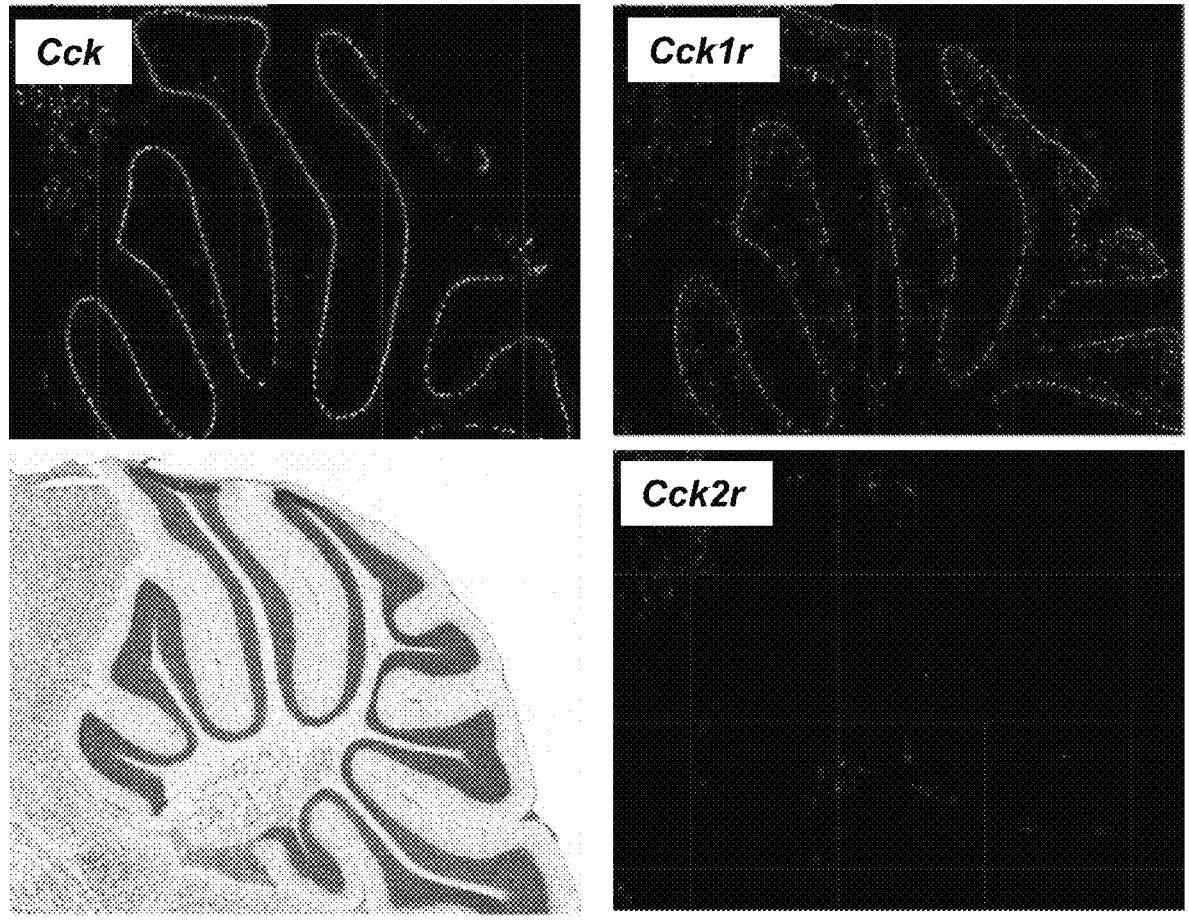

FIG. 12. Cerebellar Cck and CckRr Expression. The representative ISH expression patterns for Cck, Cck1r, and Cck2r from the Allen Brain Atlas (http://www.brain-map.org/) are presented.

Figure 13:
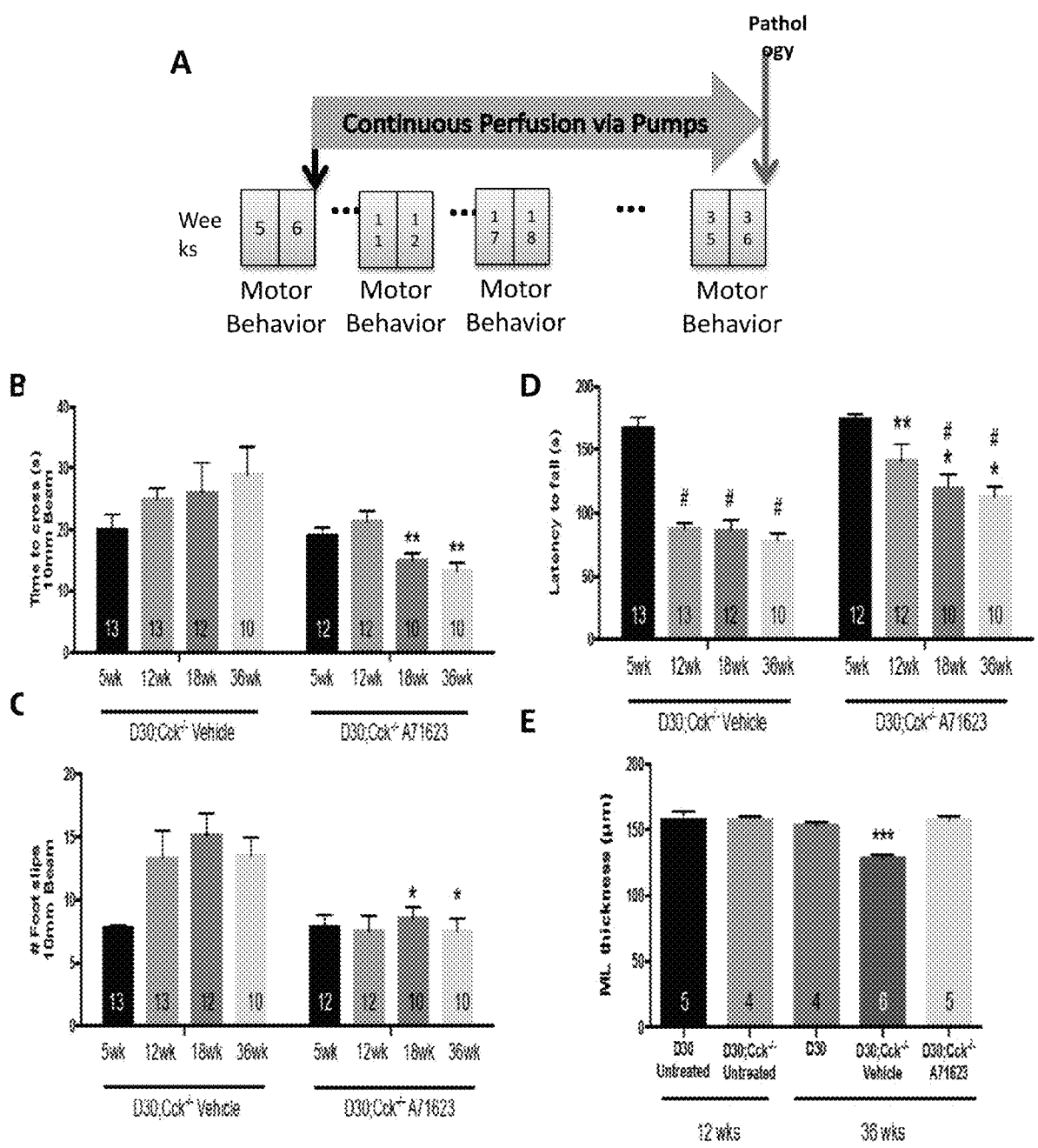

FIG. 13. D30;Cck$^{-/-}$ mice treated with Cck1R agonist A71623 are protected against disease progression. (A) Treatment Timeline. A71623 was administered from 6 weeks to 36 weeks via osmotic minipump implanted intraperitoneally (1 mg/kg/day) (B) D30;Cck$^{-/-}$ mice treated with A71623 cross the balance beam significantly faster, and with fewer foot slips (C) compared to Vehicle-treated animals, beginning at 18 weeks of age. (D) A71623-treated mice perform better on the rotarod test for motor coordination compared to vehicle-treated mice, beginning at 12 weeks. N's are represented in the bars. Two-way ANOVA, *p<0.05 compared to Vehicle, #p<0.05 compared to 5 wk (E) A71623 protects against progressive Purkinje Cell atrophy. One-way ANOVA, ***p<0.001

Figure 14:
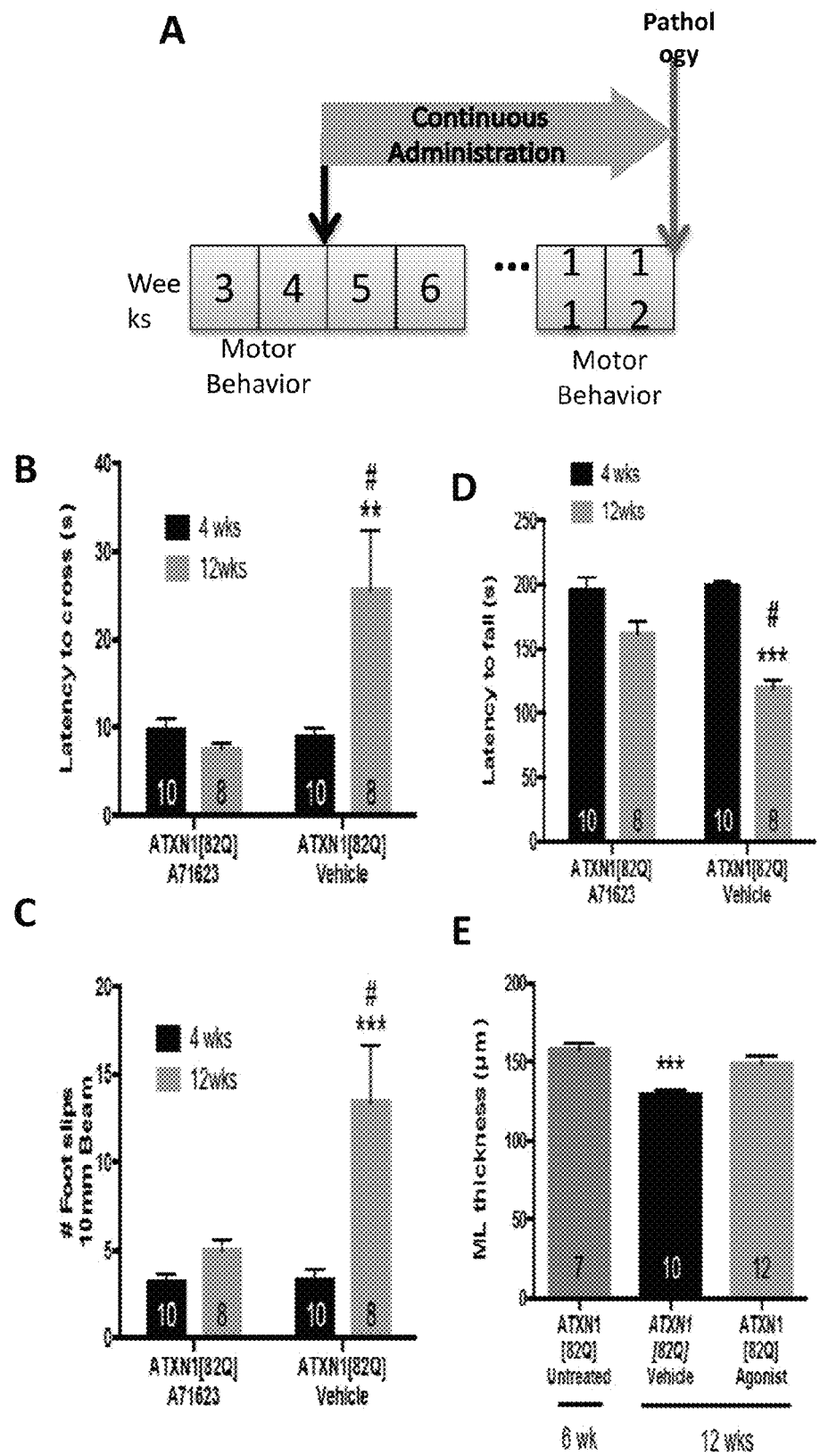

FIG. 14. ATXN1[82Q] mice treated with A71623 are protected against disease progression. (A) Treatment timeline. Baseline behavior tests were run from 3-4 weeks of age. A71623 or Vehicle was continuously administered from 5 weeks to 12 weeks via osmotic minipump intraperitoneally (1 mg/kg/day). (B) and (C) Balance Beam. Vehicle treated mice performed significantly worse on the balance beam from 4 weeks to 12 weeks, while the A71623-treated mouse behavior did not significantly change. (D) Rotarod test for motor coordination. Vehicle-treated mice performed significantly worse from 4 weeks to 12 weeks, while A71623-treated mice did not significantly change. Two-way ANOVA with Tukey's post hoc test. N's are represented in bars. p<0.01, *p<0.001 compared to A71623. #p<0.05 compared to 4 wks. (E) ML thickness in 6 wk old untreated ATXN1[82Q] mice and ATXN1[82Q] mice treated with A71623 or vehicle continuously from 6 weeks to 12 weeks. One-way ANOVA, ***p<0.001 compared to 6 wk untreated ATXN1[82Q] mice.

Figure 15:
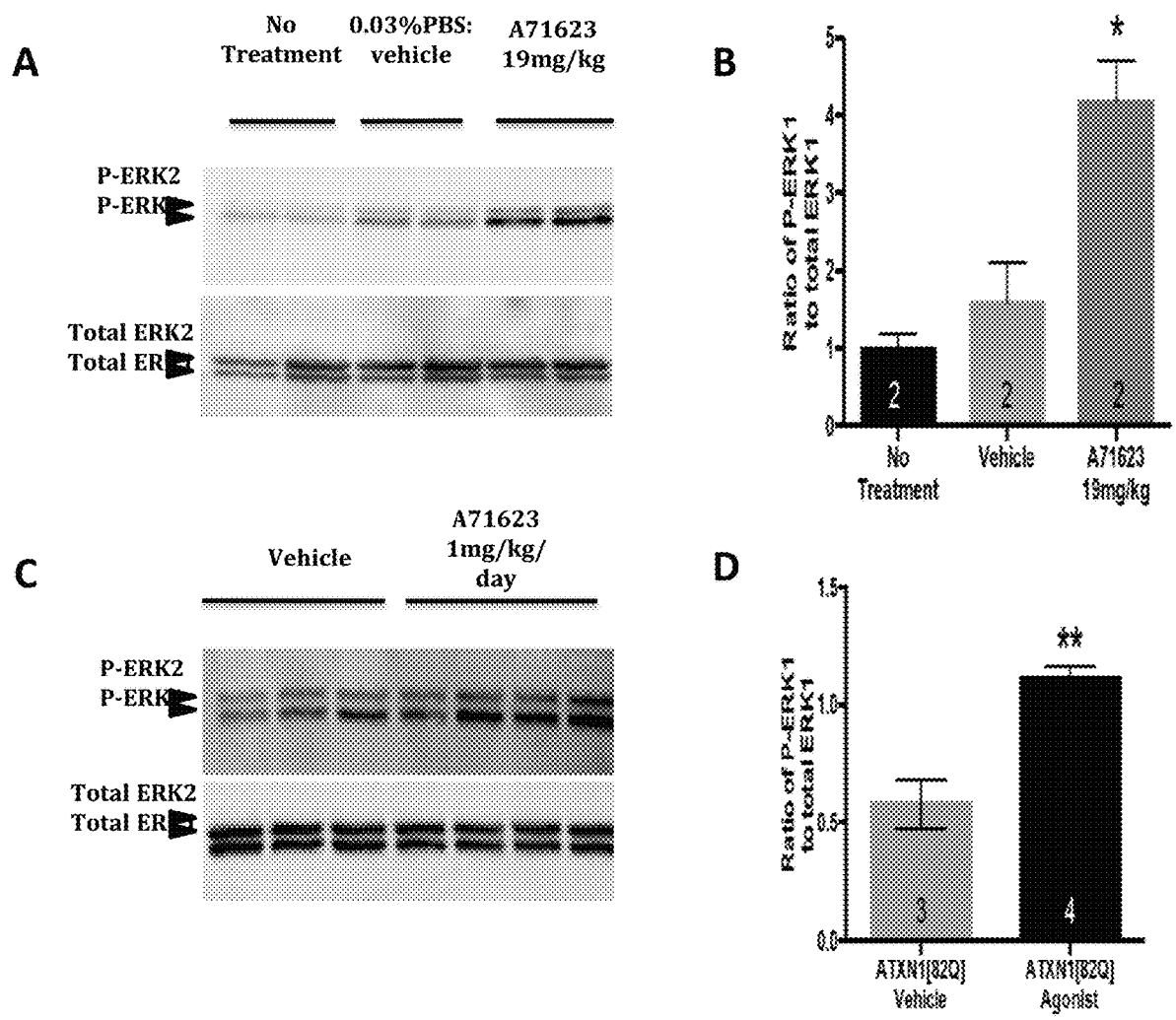

FIG. 15. P-Erk1/2, a target of the Cck1R, is increased in response to A71623 administration. (A) Representative western blot image of cerebellar lysate 6 hours following a single bolus injection of A71623 (19 mg/kg) intraperitoneally. (B) Quantification of the blot in (A) via densitometry. One-way ANOVA, *p<0.05 significantly different from no treatment (C) Western blot for P-ERK1/2 from cerebellar lysates of ATXN1[82Q] animals from FIG. 14, treated from 4-12 weeks with either A71623 or Vehicle. (D) Densitometry quantification of the western blot in (C). Student's t test, **p<0.01 significantly different from vehicle.

DETAILED DESCRIPTION OF ILLUSTRATIVE EMBODIMENTS

Spinocerebellar ataxias (SCAs) and other cerebellar ataxia disorders occur when the Purkinje Cells of the cerebellum degenerate and die, leading to difficulty in coordinating movement and balance. Conventional treatments for ataxias are aimed at alleviating symptoms since no cure is known. Upregulating the gene Cck in a mouse model of Spinocerebellar Ataxia Type 1 (SCA1) can delay and/or inhibit disease progression. When Cck or the Cck1 receptor (Cck1R) is knocked out in these mice, the mice exhibit progressive ataxia and Purkinje Cell degeneration and death. The Cck1R agonist A71623 can activate the Cck1R pathway in two different mouse models of SCA1 and inhibited progression of disease. Because of the effectiveness of the agonist treatment and the location of the Cck1R on Purkinje Cells of the cerebellum, the Cck-Cck1R pathway represents a pathway to maintain Purkinje Cell function and/or inhibit Purkinje Cell atrophy and death.

SCA1 is a fatal neurodegenerative disorder that is caused by a CAG expansion encoding a polyglutamine stretch in the protein ATXN1. RNA sequencing was used to profile cerebellar gene expression in mice with ataxia and progressive pathology and compared the gene expression profiles to those from animals having ataxia in absence of Purkinje cell progressive pathology. Weighted Gene Coexpression Network Analysis of the cerebellar expression data revealed two gene networks that significantly correlated with disease and have an expression profile correlating with disease progression ATXN1[82Q] Purkinje cells. The Magenta Module provides a signature of suppressed transcriptional programs reflecting disease progression in Purkinje cells, while the Lt Yellow Module, reflects transcriptional programs activated in response to disease in Purkinje cells as well as other cerebellar cell types. Furthermore, upregulation of cholecystokinin (Cck) and subsequent interaction with the Cck1 receptor may be involved in the lack of progressive Purkinje cell pathology in Pcp2-ATXN1[30Q]D776 mice.

Functional genomics can be applied to the study of the CNS and neurodegenerative disease. Such studies can help define the molecular settings of different regions and across different cell types within the CNS. Yet, delineation of disease transcriptional signatures—i.e., elucidating which alterations in gene expression contribute to a disease process—remains a challenge. Distinguishing changes in expression that drive disease progression from those that are a result of disease, as well as identifying protective pathways whose activation mitigate disease, can allow one to identify potential therapeutic targets.

Among inherited neurodegenerative diseases are those caused by expansion of a CAG nucleotide repeat encoding a stretch of glutamines in the protein, the polyglutamine (polyQ) diseases. The polyQ neurodegenerative disease spinocerebellar ataxia type 1 (SCA1) is a lethal, progressive, autosomal dominant disorder caused by a CAG expansion in the Ataxin-1 (ATXN1) gene. SCA1 patients typically display loss of coordination of the limbs and trunk, unstable gait, dysarthria, and nystagmus. A prominent and consistent SCA1 pathological feature is the loss of cerebellar Purkinje cells (PCs).

Several conserved sequence motifs in the ATXN1 protein, as well as cellular molecules that interact with ATXN1, indicate that ATXN1 functions in the nucleus as a regulator of transcription and RNA-processing. One such motif is the ATXN1/HBP1 (AXH) domain, residues 567-689 that folds into an OB-fold, forming putative RNA-binding and protein-protein interaction surfaces. Several transcription regulators including SMRT, Gfi-1, Capicua, and the Rora/Tip60 complex interact with ATXN1 via its AXH domain. Importantly, polyQ expanded ATXN1 lacking the AXH domain is no longer pathogenic.

Toward the C-terminus from the AXH domain is another stretch of highly conserved overlapping sequence motifs in ATXN1. Among these are a nuclear localization signal (NLS) at amino acids 771-774, which is involved in pathogenesis, and a phosphorylation site at Ser 776 (S776). Placing a non-phosphorylatable Ala at position 776 renders ATXN1[82Q] nonpathogenic, perhaps by enhancing the clearance of ATXN1 and/or by decreasing the interaction of ATXN1 with RBM17 a splicing factor. Placing an Asp at position 776 mimics enhances ATXN1/RBM17 interaction and Purkinje Cell pathogenesis of ATXN1[82Q], and transforms wild type ATXN1[30Q] into a pathogenic protein. While mice expressing ATXN1[30Q]-D776 manifest severe ataxia from an early age—i.e. as severe as ATXN1[82Q] animals—disease in ATXN1[30Q]-D776 does not have progressive cerebellar pathology culminating with Purkinje Cell death as seen in ATXN1[82Q] mice.

Thus, these mouse models provide a tool with which to identify pathways associated with the progressive loss of Purkinje Cells from the cerebellar cortex. Weighted Gene Coexpression Network Analysis was performed using longitudinal RNA sequence (RNA-seq) datasets on poly(A)+ RNA from cerebella of Pcp2-ATXN1[82Q] and Pcp2-ATXN1[30Q]-D776 mice at three ages representing early, moderate, and late stages of disease. The Weighted Gene Coexpression Network Analysis revealed one Purkinje Cell-enriched gene module, the Magenta Module, for which an age-dependent down regulation of its eigengene associated with disease in ATXN1[82Q] mice. In addition, expression of the cholecystokinin (Cck) gene was highly upregulated in ATXN1[30Q]D776 cerebellar RNA. Moreover, loss of Cck function in ATXN1[30Q]D776 mice enabled manifestation of progressive Purkinje Cell pathology, indicating that elevated Cck expression in ATXN1[30Q]D776 mice is protective against progressive disease.

Overview of ATXN1 Mouse Lines and Data Production

To identify cellular pathways contributing to SCA1-like disease in the cerebellum of ATXN1 transgenic mice, RNA-seq was used to profile expression. The mice used in this study had ATXN1 transgene expression directed specifically to Purkinje Cells using an 850 bp portion of the 5' upstream region from the Pcp2/L7 gene (Vandaele et al., 1991, *Genes Develop*. 5:1136-1148; Burright et al., 1995, *Cell* 82:937-948). Transgenic lines used included previously described ATXN1[82Q] (line B05, expressing ATXN1 with a pure $(CAG)_{82}$ repeat tract (SEQ ID NO:4)) and ATXN1[30Q] (line AO2, expressing ATXN1 with an interrupted $(CAG)_{12}$-CAT-CAG-CAT-$(CAG)_{15}$ (SEQ ID NO:3) repeat tract) (Burright et al., 1995, *Cell* 82:937-948), along with ATXN1 [30Q]D776 (line 2) mice that express ATXN1 with an unexpanded human polyQ 30-repeat tract, $(CAG)_{12}$-CAT-CAG-CAT-$(CAG)_{15}$, and a potentially phospho-mimicking Asp residue at position 776 (Duvick et al., 2010, *Neuron* 67:929-935). Like ATXN1[82Q] mice, ATXN1[30Q]D776 animals develop severe ataxia from an early age. However, in contrast to the progressive Purkinje cell pathology displayed by ATXN1[82Q] mice, pathology in ATXN1[30Q] D776 mice fails to progress beyond that typical of a midstage in ATXN1[82Q] animals. ATXN1[30Q]D776 Purkinje Cell pathology does not advance to cell death.

RNA-seq was performed on cerebellar RNA isolated from ATXN1 transgenic and wild type/FVB/NJ (wt) animals at 5 weeks, 12 weeks, and 28 weeks of age; ages corresponding to mild, moderate, and severe ataxia, respectively, in ATXN1 [82Q] mice but prior to onset of Purkinje cell death. In the case of ATXN1[30Q] mice, cerebellar RNA was isolated from five-week-old animals. Cerebellar RNA samples had RNA integration numbers (RINs) ranging from 7.9-9.3 with an average RIN of 8.7 (Table 3). Using three biological replicates/genotype, a total of 1.5 billion paired-end reads were generated with a minimum of 27.5 million reads/genotype at each age. Following data quality control and prepping, the samples were mapped to the UCSC mm10 mouse annotated genome. Between 70-90% read pairs were correctly mapped, with most samples having a greater than 80% mapping efficiency.

Overview of Cerebellar Gene Expression Changes in ATXN1 Mice

As a first step in analysis of the ATXN1 mouse cerebellar RNA-seq data, a principal component analysis (PCA) was performed (FIG. 1A). This analysis showed that data tended to cluster into three broad groups correlating with disease status. One large cluster included all samples from 5-week-old ATXN1 transgenic animals (ATXN1[30Q], ATXN1 [30Q]D776, and ATXN1[82Q] mice) and wt cerebellar samples at all ages—i.e., samples from all unaffected and mildly affected animals. A second cluster consisted of 12-week samples from moderately affected mice, ATXN1 [82Q] and ATXN1[30Q]D776. The third cluster included samples from severely ataxic 28 week ATXN1[82Q] and ATXN1[30Q]D776 mice. PCA analysis failed to distinguish changes in gene expression in ATXN1[82Q] mice having a disease with progressive pathology from ATXN1[30Q]D776 animals where disease lacked progressive Purkinje cell pathology (Duvick et al., 2010, *Neuron* 67:929-935).

Next, RNA-seq data were evaluated in pairwise comparisons using CuffDiff (Trapnell et al., 2012, *Nature Protocols* 7:562-578). Upon comparing ATXN1[82Q] and ATXN1 [30Q]D776 cerebellar gene expression data with wt at 5 weeks, 12 weeks, and 28 weeks of age, the majority of ATXN1[82Q] and ATXN1[30Q]D776 significant differences were genes downregulated in comparison to wt (FIG. 7A). This was particularly the case for the ATXN1[82Q]

versus wt comparisons at 5 weeks and 12 weeks of age. While the absolute number of significant changes in gene expression increased with age in ATXN1[82Q] vs. wt mice, the peak absolute number of ATXN1[30Q]D776 expression changes was found in 12-week-old cerebella that decreased considerably in 28-week-old ATXN1[30Q]D776 samples.

To assess changes in expression within each genotype as mice aged, expression changes were compared within ATXN1[82Q], ATXN1[30Q]D776, and wt cerebella between 5 weeks, 12 weeks, and 28 weeks of age (FIG. 7B). Both ATXN1[82Q] and ATXN1[30Q]D776 samples showed a greater number of genes whose expression changed across the three ages than was seen in wt samples. In ATXN1[82Q] mice between 5 weeks and 12 weeks, the number of genes downregulated far out-numbered genes upregulated in expression. This pattern reversed between 12 weeks and 28 weeks in ATXN1[82Q] mice, where an increase in the total number of genes with expression changes led to more genes being upregulated than downregulated. The pattern of gene expression change in ATXN1[30Q]D776 mice between 5 weeks and 12 weeks of age was very similar to that seen in ATXN1[82Q] mice both in terms of the number of genes whose expression changed and with downregulated genes out numbering upregulated genes. In contrast to the gene expression pattern In ATXN1[82Q] cerebella between 12 weeks and 28 weeks, in ATXN1[30Q]D776 mice the overall number of genes whose expression changed was decreased. This was largely due to a reduction in the number of genes with a downregulated pattern of expression between 12 weeks and 28 weeks. Thus, the overall similarity in the pattern of gene expression changes in the ATXN1[82Q] and ATXN1[30Q]D776 mice in the 5-12 week age span is consistent with the finding that both ATXN1 mice develop severe ataxia and initial signs of Purkinje Cell atrophy during this period. On the other hand, absence of a decrease in downregulated genes between 12 weeks and 28 weeks in ATXN1[30Q]D776 compared to ATXN1[82Q] cerebella correlates with an absence of a progressive Purkinje Cell pathology in ATXN1[30Q]D776.

SCAT Mouse Cerebellum Gene Coexpression Networks

Weighted Gene Coexpression Network Analysis (WGCNA) was applied to RNA-seq data from ATXN1 [82Q], ATXN1[30Q] and wt mice at 5 weeks, 12 weeks, and 28 weeks (Zhang and Horvath, 2005, *Genet Mol Biol* 4:article 17; Langfelder and Horvath, 2008, *BMC Bioinformatics* 2008, 9:559). This allows one to identify gene sets whose expression significantly correlated with one another across the three ages. Nineteen modules were detected with two, Magenta and Lt Yellow, being highly significantly associated with ataxia (t-test, adjusted p-values of $8 \times 10^{-9}$ and $1 \times 10^{-6}$, respectively; FIG. 1B, Table 4, and Table 5).

Figure 2:
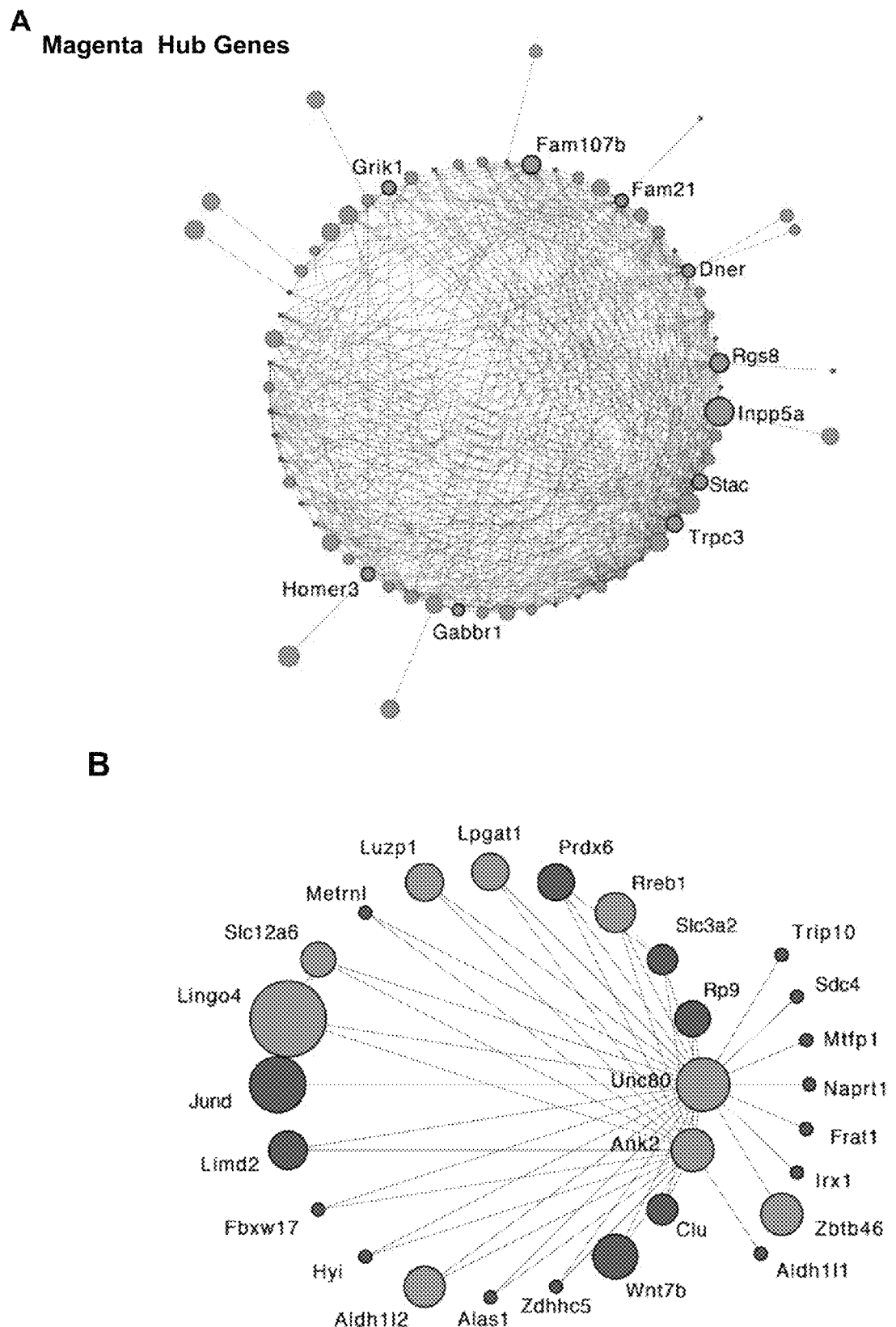
FIG. 2. WGCNA Modules Significantly Associated with Ataxia in ATXN1 Mice. For clarity only the most highly connected members of each module are depicted. Size of the circles is scaled by the absolute value of the mean $\log_2$-fold change between ATXN1[82Q] and wt/FVB, and between ATXN1[30Q]D776 and wt/FVB. (A) The Magenta network. Green are genes significantly down-regulated ATXN1[82Q] and ATXN1[30Q]D776 vs wt/FVB cerebella. The top 10 Magenta hub genes (Table 6), those with the highest intramodular connectivity, are in bold. (B) The Lt Yellow network Hub genes. Grey indicts genes whose expression either did differ significantly from wt/FVB or differed in opposite directions in ATXN1[82Q] and ATXN1[30Q]D776 vs wt/FVB cerebella.

Connectivity diagrams were generated depicting genes with the highest connectivity (hubs) within each network to identifying genes and pathways in the two ataxia-associated WGCNA modules. For the Magenta Module, all hub genes were down-regulated in ATXN1[82] and ATXN1[30Q]D776 cerebella relative to wt. Of the ten most connected hub genes (FIG. 2A), all are highly expressed by Purkinje Cells with nine being expressed exclusively by Purkinje Cells (FIG. 8). Moreover, eight of the most connected hubs encode proteins involved in signal transduction (Table 6). In contrast, Lt Yellow network hub genes included down-regulated and up-regulated genes (ATXN1[82Q] and ATXN1[30Q]D776 cerebella relative to wt) and included genes encoding proteins with a variety of functions (FIG. 2B).

To further query the ataxia associated WGCNA gene Modules for biological meaning, Ingenuity Pathway Analysis (IPA) was performed. IPA of the Magenta Module revealed ATXN1 to be the most significant (p-value of $5.91 \times 10^{-8}$) upstream regulator of this module (Table 7), indicating that changes in Magenta Module gene expression are linked to ATXN1. IPA further showed that the most significant canonical pathways were all signaling pathways. The two most significant were synaptic long-term depression (p-value $1.49 \times 10^{-5}$) and glutamate receptor signaling (p-value $2.7 \times 10^{-4}$) (Table 4), both of which have previously been implicated in pathogenesis of SCA1 and other ataxias.

IPA of the ATXN1 mouse cerebellar Lt Yellow Module revealed canonical pathways and upstream regulators not previously implicated in SCA1 or other neurodegenerative diseases (Table 7). The most significant IPA pathway was the planar cell polarity (PCP) signaling pathway (p-value of $1.45 \times 10^{-4}$). PCP signaling is a noncanonical pathway in which some members of the Wnt family activate a β-catenin independent pathway well known for its role in the organization of cell sheets during development, particularly in *Drosophila*. However, PCP signaling also is a regulator of neural functions including, for example, axonal guidance, dendrite maturation, stem cell development, and/or neuron survival. The most significant (p-value of $1.123 \times 10^{-4}$) upstream regulator of the Lt Yellow Module identified by the IPA was the Jun-protooncogene-D transcription factor, JunD.

Figure 3:
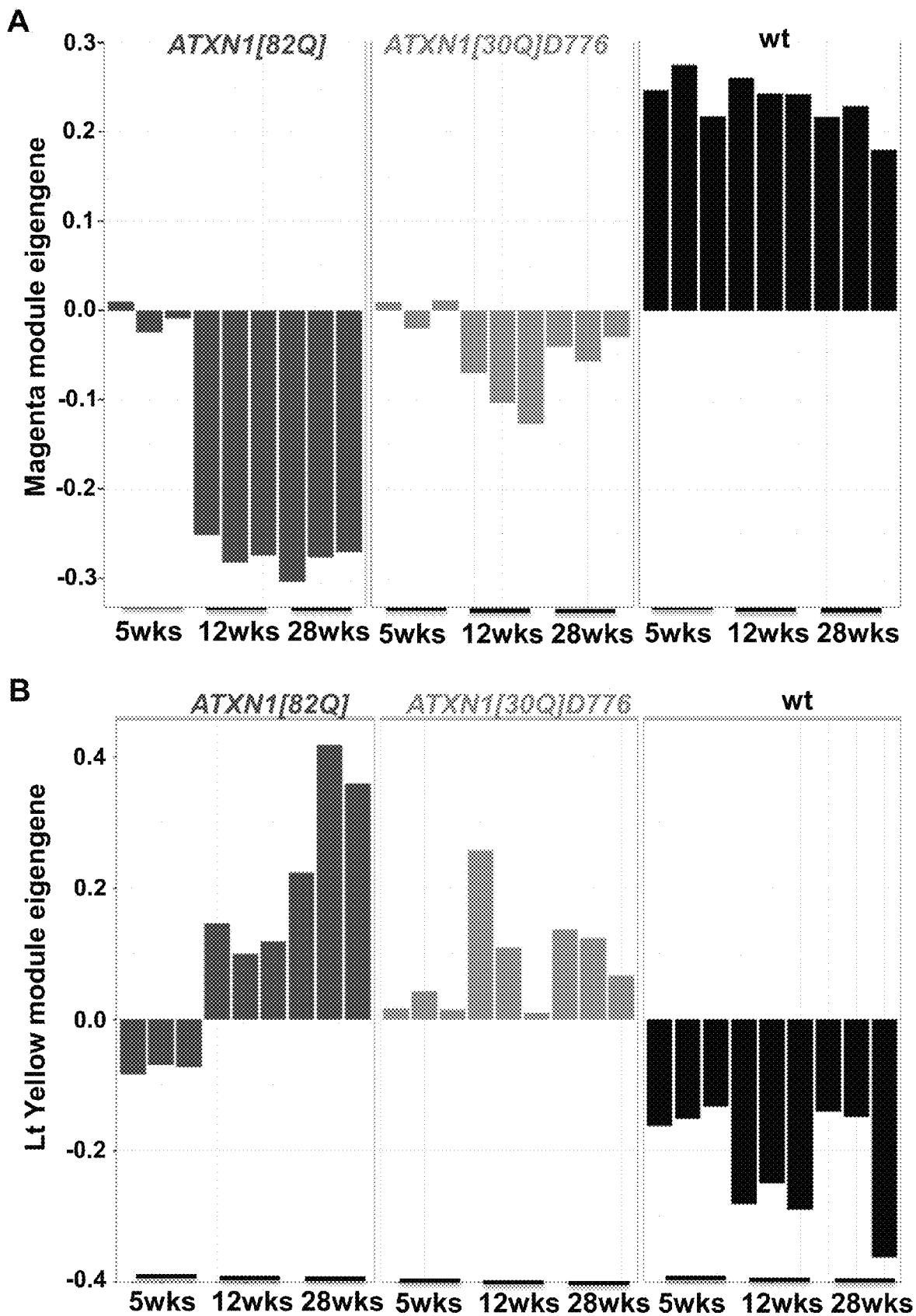
FIG. 3. (A) Magenta Module eigengene changes in ATXN1[82Q], ATXN1[30Q[D776, and wt (FVB/NJ) with increasing age: 5 weeks, 12 week, and 28 weeks. (B) Lt Yellow Module eigengene changes in ATXN1[82Q], ATXN1[30Q[D776, and wt with increasing age: 5 weeks, 12 weeks, and 28 weeks. See Table 4 and Table 5.

A detailed assessment of the co-expression pattern of RNAs across the two disease-associated mouse SCA1 WGCNA cerebellar modules was summarized with a single representative expression profile, the eigengene (FIG. 3). The Magenta eigengene was lower at all ages in the ATXN1 transgenic lines that develop ataxia, ATXN1[82Q] and ATXN1[30Q]D776, compared to wt cerebella (FIG. 3A). While the Magenta eigengene remained constant with age in wt and ATXN1[30Q]D776 cerebella, in ATXN1[82Q] cerebella the Magenta eigengene decreased substantially from 5 weeks to 12 weeks of age and remained low in 28-week-old ATXN1[82Q] cerebella. Thus, the cerebellar Magenta Module eigengene correlated with a key phenotype difference between ATXN1[82Q] and ATXN1[30Q]D776 mice— i.e., the progressive nature of disease in ATXN1[82Q] mice. Moreover, the failure of the Magenta eigengene to decrease with age in ATXN1[30Q]D776 cerebellar RNA supports the conclusion that changes in gene expression within this module reflect a progressive disease phenotype.

In contrast to the Magenta Module, the Lt Yellow Module eigengene was somewhat higher in ATXN1[82Q] and ATXN1[30Q]D776 cerebellar RNA compared to age matched wt samples (FIG. 3B). Moreover, the Lt Yellow eigengene increased with age in ATXN1[82Q] cerebellar RNA and remained essentially constant in ATXN1[30Q] D776 and wt samples. Thus, while the cerebellar Lt Yellow Module eigengene correlated with disease progression in ATXN1[82Q] mice, its change with age in ATXN1[82Q] increased rather than decreased as seen in the Magenta Module, suggesting that the underlying biology encoded by these two disease-associated modules differs.

Disease-Associated Co-Expression Modules Differ in Cerebellar Cell Type Markers

Several lines of evidence indicate that the Magenta Module is enriched for genes preferentially expressed by Purkinje Cells, while the Lt Yellow Module has a more substantial representation of genes expressed by multiple cerebellar cell types (Table 1). First, the Magenta Module showed highly significant overlap (p-value of $4.5 \times 10^{-16}$) with the cerebellar M6D WGCNA module identified from human brain microarray data. The M6D module largely includes genes differentially expressed by Purkinje Cells relative to other cerebellar cell types. Of the ten strongest members of M6D, four genes overlapped with the Magenta Module, including Calb1 (the strongest member of M6D), Itpr1, Plxdc1, and Pcp4. In total, 19 genes overlapped between the human cerebellar M6D network and the mouse Magenta Module (Table 1). Of the 342 genes in the mouse ATXN1 cerebellar Magenta Module, 94 were among RNAs whose translation is enhanced in Purkinje Cells (Table 1). The Lt Yellow Module, in contrast, had no genes that overlapped with the human cerebellar M6D Module and only one gene, lysophosphatidylglycerol acyltransferase 1 (Lpgat1), encoding RNA with enhanced PC translation (Table 1 and Table 5).

TABLE 1

Expression of ATXN1 Cerebellar WGCNA Module Genes ISH Pattern (Allen Brain Atlas)

| Module (adjusted p-value) | Genes | Overlap-M6D PC Network* | PC-enriched Translation** | I PC-exclusive | II Multiple Cell Types | I/II |
|---|---|---|---|---|---|---|
| Magenta | 342 | 19 | 94 (27%) | 175 (51%) | 31 (9%) | 5.6 |
| Lt Yellow | 35 | 9 | 1 (3%) | 11 (31%) | 8 (22%) | 1.4 |

*Oldham et al., 2008, *Nat. Neurosci.* 11: 1271-1282
**Doyle et al., 2008, *Cell* 135: 749-762

To assess the cerebellar cellular expression pattern of genes within the Magenta and Lt Yellow Modules, in situ hybridization (ISH) data from the Allen Brain Atlas was utilized (Len et al., 2007, *Nature* 445:168-176). This analysis revealed Purkinje Cell-exclusive expression for 175 Magenta Module genes and 52 genes showing expression in multiple cerebellar cell types (Table 1 and FIG. 8). To identify genes most strongly correlated with the eigengene expression in the most severely affected mice, 79 genes of the Magenta Module were identified whose correlation with the eigengene for ATXN1[82Q] samples across all time points was 0.9 or greater. Of these genes, 61 (77%) had evidence of a Purkinje Cell-enriched pattern of expression and 16 were expressed by a wider range of cerebellar cell types. Of the 35 Lt Yellow Module genes, 11 genes showed Purkinje Cell-exclusive expression by in situ hybridization (ISH), eight with Purkinje Cell-enriched expression, and eight were equally expressed in multiple cell types. The number of genes in the Magenta Module whose expression was exclusive to Purkinje Cells was 5.6-fold greater than the number of genes whose expression was distributed more uniformly among multiple cerebellar cell types (Table 1).

In contrast, analysis of the cerebellar cellular expression pattern of Lt Yellow module genes revealed that genes with a Purkinje Cell-exclusive pattern of expression was only 1.4-fold greater than those expressed to a similar degree by other cerebellar cell types (Table 1 and FIG. 9). Thus, compared to the Lt Yellow Module, the relative number of genes within the Magenta Module expressed specifically in Purkinje Cells was considerably greater. Based on these data, the Magenta Module is enriched for genes preferentially expressed by Purkinje Cells while a greater proportion of Lt Yellow Module genes are expressed more widely by multiple cerebellar cell types.

The Disease-Associated WGCNA Magenta Module is Enriched for Genes Regulated by ATXN1 Interacting Protein Cic ATXN1 protein interactors include regulators of transcription such as, for example, the Capicua homolog (Cic), SMRTER, GFI-1, and RORα/Tip60. To examine whether genes of the Magenta and Lt Yellow Modules are be regulated by these ATXN1-interacting transcriptional factors, sequences 2.0 kb upstream of the transcription start site of each gene in the Magenta and Lt Yellow Modules were extracted from the hg19 human genome reference and assessed for de novo motifs using MEME, DREME, and CentriMo (Machanic and Bailey, 2011, *J. Neurosic.* 18:5508-5516). De novo motifs identified were compared with known motifs in the JASPAR and UniPROBE databases. RORα/Tip60 and Gfi-1 binding motifs were not significantly enriched in the upstream regions of Magenta or Lt Yellow genes. Cic and SMRT binding motifs were not in these databases. Screening was performed, however, for two known Cic binding motifs, TGAATGAA (SEQ ID NO:1) and TGAATGGA (SEQ ID NO:2). The promoter sequences (2 kb upstream of TSS) of each gene in the two modules were extracted from human reference hg19 genome. Sequence Fasta files were used as input to the FIMO software (Grant et al., 2011, *Bioinformatics* 27(7):1017-1018) to scan sequence database for matches to each motif. As a control, each upstream sequence was randomly shuffled and screened for the binding motifs. The results showed that a highly significant number of Magenta Module genes have either one or both of the Cic binding motifs TGAATGAA (SEQ ID NO:1) and TGAATGGA (SEQ ID NO:2) in their upstream region with p values of $2.73 \times 10^{-12}$ and $5.85 \times 10^{-10}$, respectively (Table 2 and Table 8). Analysis of Lt Yellow Module genes revealed only the number of TGAATGGA (SEQ ID NO:2) motifs reached significance with a p value of 0.005 (Table 2). These results suggest that the Magenta Module is enriched for genes whose expression is regulated by the ATXN1-interacting transcription factor Cic.

TABLE 2

Presence of Cic-bindng Motifs in Magenta and Lt Yellow Module

| Cic Binding Motif | Module | | Control* | p value |
|---|---|---|---|---|
| TGAATGAA (SEQ ID NO: 1) | Magenta | | | |
| Genes motif present | | 149 | 61 | $2.73 \times 10^{-12}$ |
| Genes motif not present | | 190 | 278 | |
| TGAATGGA (SEQ ID NO: 2) | Magenta | | | |
| Genes motif present | | 180 | 100 | $5.85 \times 10^{-10}$ |
| Genes motif not present | | 159 | 239 | |
| TGAATGAA (SEQ ID NO: 1) | Lt Yellow | | | |
| Genes motif present | | 5 | 6 | ns |
| Genes motif not present | | 29 | 28 | |
| TGAATGGA (SEQ ID NO: 2) | Lt Yellow | | | |
| Genes motif present | | 18 | 7 | 0.005 |
| Genes motif not present | | 14 | 27 | |

*Randomized sequence for each gene in module were counted. Fisher's exact test was used to measure the enrichment significance of the two motifs in Magenta and Light yellow modules.

Magenta Module Purkinje Cell-Specific Genes are Down Regulated in Atxn1$^{2Q/154Q}$ Cerebella The Magenta Module is enriched in genes preferentially expressed by Purkinje Cells that seem to drive pathogenesis in ATXN1[82Q] mice. qRT-PCR was used to assess the expression of a set of Magenta genes in the cerebella of 12-week-old Atxn1$^{2Q/154Q}$ mice (Matilla et al., 1998, *J. Neurosic.* 18:5508-5516). All eight Magenta genes examined had module correlations of either greater than 0.9 or less than −0.9. Six of the genes were down-regulated in ATXN1[82Q] and ATXN1[30Q]D776 cerebellar RNA compared to age matched wt samples (Calb1, Itpr1, Inpp5a, Pcp4, Garnl3, and Rgs8), with three of these being hubs (Itpr1, Inpp5a, and Rgs8). The other two genes examined were, Syt13 and Mxra7, both up-regulated in ATXN1[82Q] and ATXN1[30Q]D776 cerebella. FIG. 10 shows that all six of the genes down-regulated in ATXN1[82Q] and ATXN1[30Q]D776 were significantly down in Atxn1$^{2Q/154Q}$ cerebellar RNA. In contrast, expression of neither of the two Magenta genes up-regulated in ATXN1[82Q] and ATXN1[30Q]D776 changed in Atxn1$^{2Q/154Q}$ mice. This conservation in expression changes between ATXN1[82Q] and ATXN1[30Q]D776 and Atxn1$^{2Q/154Q}$ mice provides further support for down-regulation of Magenta genes being involved in pathogenesis.

Elevated Cck Activates a Neuroprotective Pathway in ATXN1[30Q]-D776 Cerebella Mediated by Cck1 Receptor One potential explanation for the failure of Purkinje Cell pathology to progress in ATXN1[30Q]D776 cerebella is that a neuroprotective pathway was activated in these mice. If so, then activation of the neuroprotective pathway might be reflected by elevated expression of genes in ATXN1[30Q]D776 cerebellar RNA relative to wt and ATXN1[82Q] cerebellar RNA. Moreover, activation of a prominent pathway in ATXN1[30Q]D776 cerebella might be reflected by a gene whose expression relative to wt is higher in ATXN1[30Q]D776 and lower in ATXN1[82Q] mice. Of the 130 genes whose expression differed significantly between ATXN1[30Q]D776 and ATXN1[82Q] as well as between each and wt (FIG. 4A), 32 were upregulated in ATXN1[30Q]D776 and downregulated in ATXN1[82Q] (FIG. 4B). Of these 32, two, cholecystokinin (Cck) and collagen, type XVIII, alpha 1 (Col18a1), had expression levels of ≥3.0 FPKM. Of these, Cck was expressed at far greater levels in ATXN1[30Q]D776 compared to ATXN1[82Q] cerebella (FIG. 4B). Furthermore, qRT-PCR confirmed that Cck expression relative to wt/FVB was significantly elevated in the cerebellum of all three lines of ATXN1[30Q]D776 mice lacking progressive Purkinje Cell pathology, and decreased relative to wt in ATXN1[82Q] that have a progressive disease (FIG. 4C).

To assess whether Cck has a role in cerebellar function/dysfunction, Cck$^{-/-}$ mice (Lay et al., 1999, *Develop. Dynamics* 216:190-200) were assessed for altered cerebellar morphology and neurological status. According to calbindin immunostaining at 20 weeks and one year of age, Purkinje Cells in Cck$^{-/-}$ mice were indistinguishable from those in age-matched wt mice (FIG. 11A). While Cck$^{-/-}$ mice showed no loss of Purkinje Cells out to one year of age in Cck$^{-/-}$ cerebella (FIG. 11B), there was a slight and significant decrease in thickness of the cerebellar molecular layer between 20 weeks and one year of age (FIG. 11C). In addition, qRT-PCR analysis revealed a significant reduction in expression of a Purkinje Cell marker calbindin (Calb) in cerebellar RNA from 1-year-old Cck$^{-/-}$ mice (FIG. 11D). These analyses showed that while loss of Cck adversely impacted cerebellar morphology and function, it did not cause severe atrophy and loss of Purkinje Cells.

Figure 5:
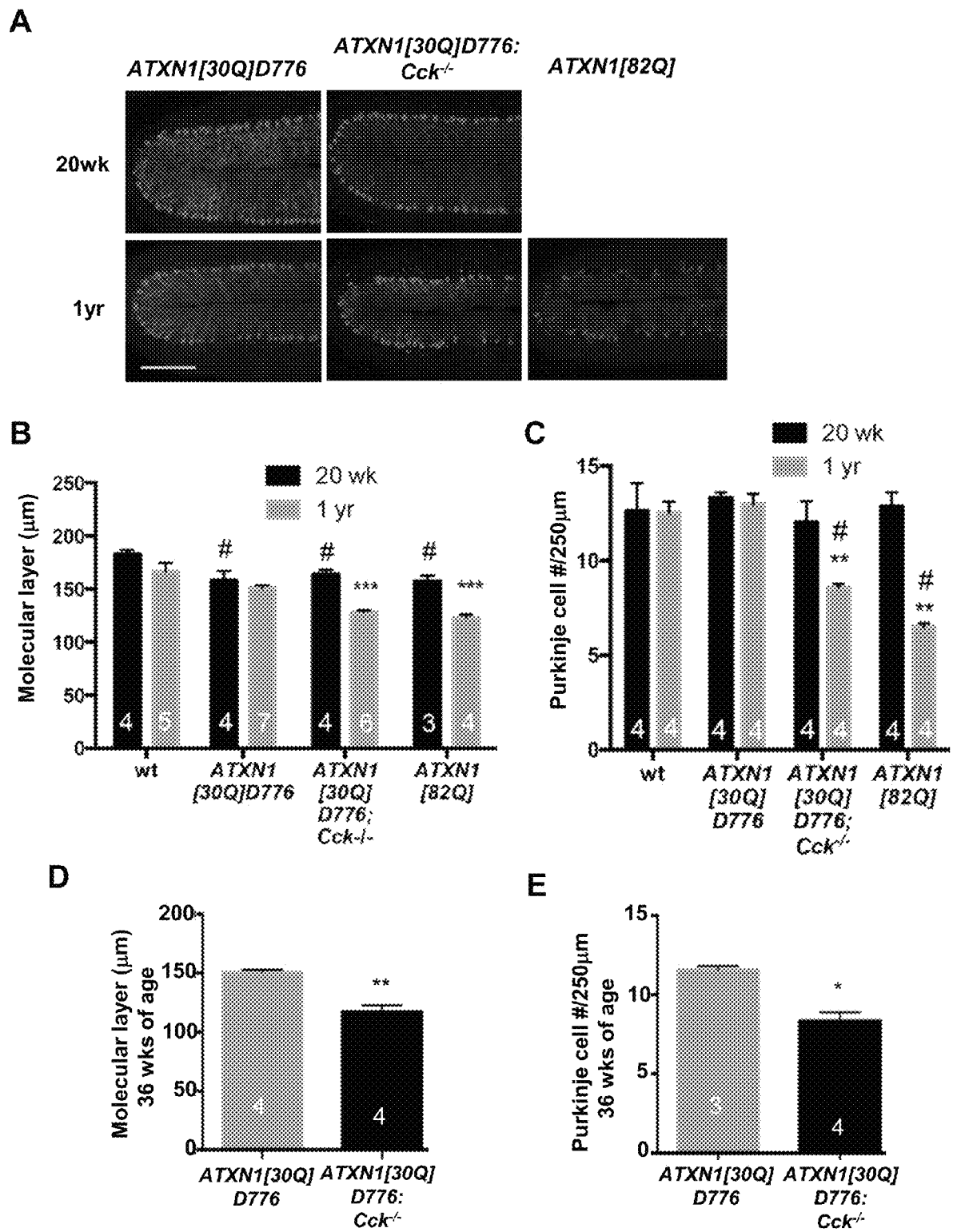
FIG. 5. Elevated Cck expression is protective against progressive Purkinje cell atrophy and death in ATXN1[30Q]D776 mice. (A) Representative images depicting primary cerebellar fissure showing Purkinje Cell morphology revealed by calbindin immunostaining. Scale bar, 200 µm applies to all images in this panel. (B) Changes in cerebellar molecular layer thickness for examined genotypes at 20 weeks of age vs. 1 year of age. (C) Purkinje Cell counts for examined genotypes at 20 weeks of age vs. 1 year of age. Calbindin-positive Purkinje Cell bodies were counted within the primary fissure per 250 µm. Data in (B) and (C) are represented as mean, ±SEM. Two-Way ANOVA, Tukey post-hoc test. # indicates $p<0.01$ compared to wt. $*p<0.05$, $p<0.01$, and $*p<0.001$ comparing 1 year to 20 wks. Numbers of cerebella analyzed per genotype and age are indicated within each bar. (D) Changes in cerebellar molecular layer thickness at 36 weeks of age in ATXN1[30Q]D776 and ATXN1[30Q]D776: $Cck^{-/-}$ mice.±SEM, Student's t-test. $**p<0.002$. (E) Purkinje cell counts for per 250 µM at 36 weeks of age in ATXN1[30Q]D776 and ATXN1[30Q]D776: $Cck^{-/-}$ mice. Data mean, ±SEM. Student's t-test. $*p<0.01$.

Next, whether elevated Cck expression could inhibit progression of Purkinje Cell disease in ATXN1[30Q]D776 mice was assessed by crossing Cck$^{-/-}$ and ATXN1[30Q] D776 mice. Examination of cerebellar pathology in one-year-old mice revealed more extensive Purkinje Cell pathology in ATXN1[30Q]D776;Cck$^{-/-}$ mice compared to one-year-old ATXN1[30Q]D776 mice (FIG. 5A). As measured by molecular layer thickness, ATXN1[30Q]D776;Cck$^{-/-}$ mice had a progressive atrophy of Purkinje Cell dendrites from 20 weeks to 1 year of age in contrast to ATXN1[30Q] D776 mice that showed no progression in molecular layer atrophy between 20 weeks and one year of age (FIG. 5B). Moreover, progression in molecular layer atrophy with age in ATXN1[30Q]D776;Cck$^{-/-}$ mice was essentially identical to that seen in ATXN1[82Q] cerebella. Absence of Cck in ATXN1[30Q]D776 mice resulted in a progressive disease that included loss of Purkinje Cells from the cerebellar cortex (FIG. 5C). In addition, cerebella from ATXN1[30Q] D776;Cck$^{-/-}$ mice at 36 weeks of age displayed enhanced pathology compared to ATXN1[30Q]D776 animals as assessed by atrophy of the molecular layer and loss of Purkinje Cells (FIGS. 5D and 5E). Absence of Cck function in ATXN1[30Q]D776 mice resulted in a more severe and progressive Purkinje Cell pathology similar to pathology in ATXN1[82Q] mice. These results are consistent with elevated Cck expression in ATXN1[30Q]D776 mice affording protection against a form of Purkinje Cell pathology that progresses to cell death.

In the cerebellar cortex, Cck is predominately expressed by Purkinje Cells, a point further supported by in situ hybridization (ISH) data from the Allen Brain Atlas (FIG. 12). Cck, a prohormone, is processed to active peptides whose actions are mediated by two G-protein coupled receptors, Cck1R and Cck2R (first designated as Cckar and Cckbr). ISH data indicate that Cck1r is the one expressed in the adult mouse cerebellum in a Purkinje Cell-enriched manner (FIG. 12). Given the data indicating that elevated Cck can inhibit Purkinje Cells disease progression to cell death coupled with the data that Cck1r is uniquely expressed in the mouse cerebellum by Purkinje Cells, the Cck protective effect in ATXN1[30Q]D776 mice may be via the Cck1r. To test this, ATXN1[30Q]D776 mice were crossed with mice lacking either Cck1R or Cck2R. Consistent with the cerebellar cellular expression pattern of CckRs, ATXN1 [30Q]D776 mice lacking Cck1R developed a progressive Purkinje Cell pathology as assessed by atrophy of molecular layer thickness (FIGS. 6A and 6B) and loss of Purkinje Cells with age (FIG. 6C). In contrast, ATXN1[30Q]D776/Cck2R$^{-/-}$ mice showed the same lack of an age-dependent Purkinje Cell pathology as seen in ATXN1[30Q]D776 animals (FIG. 6). Based on these data, the lack of a progressive Purkinje Cell pathology in ATXN1[30Q]D776 mice is due to increased expression of Cck by ATXN1[30Q]D776 Purkinje Cells and cleavage of the proCck into a secreted peptide that activates Purkinje Cell Cck1Rs.

Figure 4:
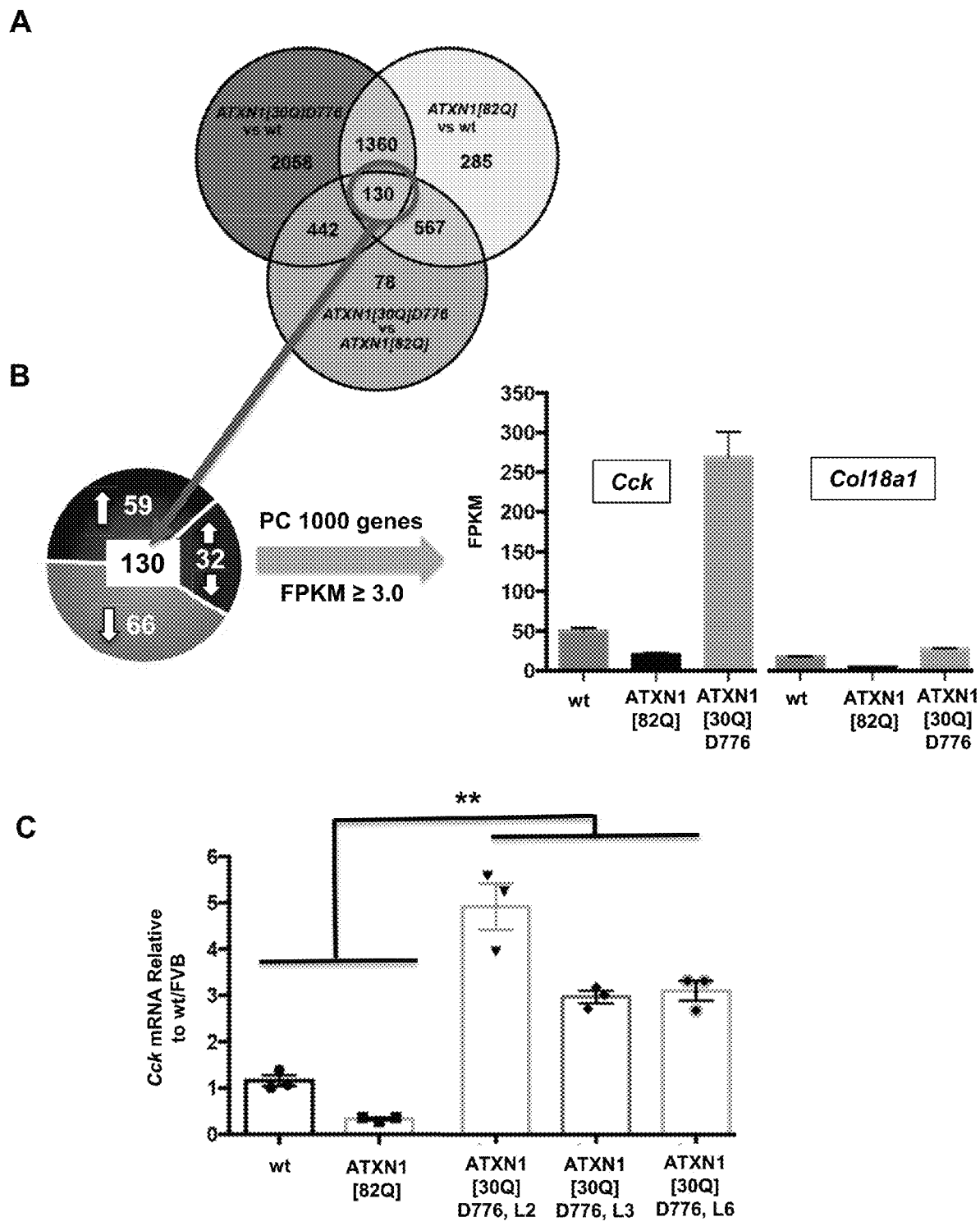
FIG. 4. Expression of cholecystokinin (Cck) is elevated in ATXN1[30Q]D776 cerebella. (A) Venn diagram depicting the total number of transcripts changed at 12 weeks of age. (B) Breakdown of the expression changes for the 130 genes with significant changes in common between ATXN1[82Q] and ATXN1[30Q]D776 cerebella. Fifty-nine genes were upregulated in both compared to wt (FVB/NJ) and 66 genes downregulated. Thirty-two genes changed in opposite directions in ATXN1[82Q] and ATXN1[30Q]D776 cerebella. Of these 32 genes, two genes (Cck and Col18a1) had expression levels of FPKM≥3.0 and enhanced translation in Purkinje cells. (C) qRT-PCR validation of elevated Cck cerebellar expression in ATXN1[30Q]D776 mice relative to other ATXN1 transgenic lines.

Thus, ATXN1 mouse cerebellar RNA-seq analyses revealed a substantial, unique, and Purkinje Cell-specific upregulation of cholecystokinin (Cck) RNA in Pcp2-ATXN1[30Q]D776 mice, in which Purkinje Cell disease is not progressive (FIG. 4). Cck, originally discovered in the gastrointestinal tract, is an abundant neuropeptide, having selective effects on specific cell types and synapses. A consequence of enhanced expression of Cck in ATXN1 [30Q]D776 Purkinje cells in relation to their lack of progressive disease was revealed by crossing ATXN1[30Q] D776 mice with mice lacking either Cck or Cck1R. Absence of either Cck or Cck1R in Pcp2-ATXN1[30Q]D776 mice resulted in a Purkinje Cell disease in which pathology progressed to cell death. The natural ligand with the highest affinity for the Cck1R is Cck-8, an octapeptide cleaved from the C-terminal portion of Cck. Thus, elevated Cck and its subsequent processing to a peptide that binds to Purkinje cell Cck1R can inhibit progression of Purkinje cell pathology in ATXN1[30Q]D776 mice.

At 11 weeks of age, the vehicle-treated ATXN1[82Q] mice took longer to cross the balance beam (FIG. 14B; Two-Way ANOVA with Tukey post-hoc test, p=0.0008), and had more foot slips than they had at three weeks (FIG. 14C; p=0.0002). Similarly, the vehicle-treated mice performed worse on Day 4 of the rotarod at 12 weeks than they had at three weeks (FIG. 14D; Two-Way ANOVA with Tukey post-hoc, p=0.0005). In contrast, mice treated with A71623, as a model Cck1R agonist, had no significant change in time to cross (p=0.8875) or number of foot slips (p=0.702) on the balance beam, and no significant change in rotarod performance on Day 4 from four week to 12 weeks of age (p=0.9984). The A71623-treated mice additionally performed better at 11-12 weeks than the vehicle-treated mice on all motor behavior measures, including time to cross (p=0.0003) and number of foot slips on the balance beam (p=0.0013), and latency to fall on Day 4 of the rotarod test (p=0.0263). These behavioral outcomes indicate that a Cck1R agonist such as A71623 can be used to successfully treat progressive motor behavior deficits.

The vehicle-treated mice at 12 weeks of age had significantly smaller ML thicknesses than six-week-old untreated ATXN1[82Q] mice (FIG. 14E; Two-way ANOVA with Tukey post-hoc, p=0.0001), whereas A71623-treated mice had no change in ML thickness by 12 weeks (p=0.2114). A71623-treated mice at 12 weeks of age have significantly thicker ML than vehicle-treated mice (p=0.002). These pathological findings indicate that a low dose of A71623 can be used to treat progressive PC degeneration.

These data indicated that a Cck1R agonist such as, for example, A71623 can decrease progressive motor behavior deficits and progressive PC atrophy in ATXN1[30Q]D776; Cck$^{-/-}$ and ATXN1[82Q] mice. ATXN1[30Q]D776;Cck$^{-/-}$ mice have a slow progressive timeline compared to ATXN1 [82Q] mice. Therefore the ATXN1[30Q]D776;Cck$^{-/-}$ mice were treated with either A71623 (0.02 mg/kg/Day) or vehicle (20 mM PBS) from six weeks to 36 weeks of age. ATXN1[82Q] mice have a faster disease progression, and the most significant change in PC pathology is seen as early as 12 weeks. Therefore, these mice were given A71623 or vehicle from four weeks to 12 weeks of age. In both progressive mouse models, treatment with a Cck1R agonist significantly decreased disease progression, as evidenced by increased maintenance of motor behavior performance and no progressive PC degeneration.

Accordingly, this disclosure describes a method of treating a subject having, or at risk of having, ataxia. Generally, the method involves administering to the subject an amount of a composition comprising a cholecystokinin receptor (Cck1R) agonist effective to ameliorate at least one symptom or clinical sign of ataxia. As used herein, the term "treat" or variations thereof (e.g., "treating" a subject) refer to reducing, limiting progression, ameliorating, or resolving, to any extent, the symptoms or signs related to a condition. In this context, the term "ameliorate" refers to any reduction in the extent, severity, frequency, and/or likelihood of a symptom or clinical sign characteristic of a particular condition. As used herein, the term "symptom" refers to any subjective evidence of disease or of a patient's condition; the term "sign" or "clinical sign" refers to an objective physical finding relating to a particular condition capable of being found by one other than the patient.

Exemplary symptoms and/or clinical signs of ataxia include but are not limited to decreased motor coordination, unsteady walking gait, increased difficulty with fine motor tasks (e.g., eating, writing, keyboarding), changes in speech (e.g., slurring, slow, and/or unusual speech rhythms), increased nystagmus (involuntary back-and-forth eye movements), increased difficulty swallowing, headaches, dizziness, fatigue, decreased balance, blurred vision, double vision, increased difficulty reading, increased difficulty following moving objects, and/or difficulty shifting gaze from one object to another.

The treatment method may be therapeutic—i.e., initiated after the subject exhibits one or more symptoms or clinical signs of the condition. Alternatively, in some embodiments the method may be prophylactic—i.e., initiated before a subject manifests a symptom or clinical sign of ataxia. Prophylactic treatment may be administered to a subject "at risk" of developing ataxia. As used herein, the term "at risk" refers to a subject that may or may not actually possess the described risk. Thus, for example, a subject "at risk" of ataxia is a subject possessing one or more risk factors associated with ataxia (e.g., genetic predisposition or medical history) even if the subject exhibits no symptoms or clinical signs of ataxia.

Accordingly, the treatment method may be performed before, during, or after the subject first exhibits a symptom or clinical sign of ataxia. Treatment initiated before the subject first exhibits a symptom or clinical sign of ataxia may result in decreasing the likelihood that the subject experiences clinical evidence of ataxia compared to a comparable subject to whom the treatment is not administered, decreasing the severity of symptoms and/or clinical signs of ataxia, and/or completely resolving the condition. Treatment initiated after the subject first exhibits a symptom or clinical sign of ataxia may result in decreasing the severity of symptoms and/or clinical signs of ataxia compared to a comparable subject to whom the treatment is not administered, and/or completely resolving the condition.

Thus, the method includes administering an effective amount of a composition that includes a cholecystokinin receptor (Cck1R) agonist to a subject having, or at risk of having, ataxia. In this aspect, an "effective amount" is an amount effective to reduce, limit progression, ameliorate, or resolve, to any extent, a symptom or clinical sign of ataxia.

As used herein, a cholecystokinin receptor (Cck1R) agonist refers to any compound that can combine with Cck1R to induce a cellular activity. An agonist may be a ligand that directly binds to Cck1R. Alternatively, an agonist may combine with a receptor indirectly by, for example, (a) forming a complex with another molecule that directly binds to the receptor, or (b) otherwise results in the modification of another compound so that the other compound directly binds to the receptor. Exemplary Cck1R agonist include, but are not limited to, A71623 (Asin et al., 1992, *Am J Physiol*, 263: R125-R135), CCK-33 (Innis R B and Synder S H, 1980, *Proc Natl Acad Sci USA*, 77:6917-6921), ARL-15849 (Simmons et al., 1998, *Pharmacol Biochem Behav*, 59:439-444), PD136450 (Blevins et al., 1994, *J Pharmacol Exp Ther*, 269:911-916), SR146131 (Bignon et al., 1999, *J Pharmacol Exp Ther*, 289:742-751), CCK-58 (Reeve et al., 2002, *Pancreas*, 25:e50-e55), [$^{125}$I]DTyr-Gly-[(Nle28,31) CCK-26-33 (Powers et al., 1988, *Int. J. Pept. Protein Res.*, 31(5):429-434), CCK-8 (Hughes et al., 1990, *Proc Natl Acad Sci USA*, 87:6728-6732), JMV180 (Kennedy et al., 1995, *Biochem. Biophys. Res. Commun.*, 213 (3):845-852), GW-5823 (Henke et al., 1997, *J Med Chem*, 40:2706-2725), Glaxo-11p (Aquino et al., 1996, *J Med Chem*, 39:562-569), GI181771X (Jordan et al., 2008, *Clin Pharmacol Ther* 83(2):281-287), gastrin-17 (Hughes et al., 1990, *Proc Natl Acad Sci USA*, 87:6728-6732), CCK-4 (Hughes et al., 1990, *Proc Natl Acad Sci USA*, 87:6728-6732), and rebamipide (Moon et al., 2004, *Eur J Pharmacol*, 505:61-66). In certain embodiments, the Cck1R agonist can include A71623. In other embodiments, the Cck1R agonist can include rebamipide.

A composition that includes the Cck1R agonist may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the Cck1R agonist, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with a Cck1R agonist without causing any undesirable biological effects or interacting in a deleterious manner with any of the other components of the pharmaceutical composition in which it is contained.

A Cck1R agonist may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, a Cck1R agonist may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the Cck1R agonist into association with a carrier that constitutes one or more accessory ingredients. In general, a formulation may be prepared by uniformly and/or intimately bringing the Cck1R agonist into association with a liquid carrier, a finely divided solid carrier, or both, and then, if necessary, shaping the product into the desired formulations.

The amount of Cck1R agonist administered can vary depending on various factors including, but not limited to, the specific Cck1R agonist, the weight, physical condition, and/or age of the subject, and/or the route of administration. Thus, the absolute weight of Cck1R agonist included in a given unit dosage form can vary widely, and depends upon factors such as the species, age, weight and physical condition of the subject, and/or the method of administration. Accordingly, it is not practical to set forth generally the amount that constitutes an amount of Cck1R agonist effective for all possible applications. Those of ordinary skill in the art, however, can readily determine the appropriate amount with due consideration of such factors.

For example, certain Cck1R agonist may be administered at the same dose and frequency for which the drug has received regulatory approval. In other cases, certain Cck1R agonists may be administered at the same dose and frequency at which the drug is being evaluated in clinical or preclinical studies. One can alter the dosages and/or frequency as needed to achieve a desired level of Cck1R agonist. Thus, one can use standard/known dosing regimens and/or customize dosing as needed.

In some embodiments, the method can include administering sufficient Cck1R agonist to provide a dose of, for example, from about 100 ng/kg to about 50 mg/kg to the subject, although in some embodiments the methods may be performed by administering Cck1R agonist in a dose outside this range. In some of these embodiments, the method includes administering sufficient Cck1R agonist to provide a dose of from about 10 μg/kg to about 5 mg/kg to the subject, for example, a dose of from about 100 μg/kg to about 1 mg/kg.

In some embodiments in which the Cck1R agonist is A71623, the method can include administering A71623 to a subject to provide a dose of from 10 μg/kg/day to 1 mg/kg/day such as, for example, from 25 μg/kg/day to 150 μg/kg/day. A dose of about 25 μg/kg/day is near the lowest dose shown to inhibit food intake after a single, bolus intraperitoneal injection. Inhibiting food intake is a well-studied behavioral consequence of Cck1R activation that is known to be, at least in part, centrally-mediated.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2 = (wt\ kg^{0.425} \times height\ cm^{0.725}) \times 0.007184$.

In some embodiments, the method can include administering sufficient Cck1R agonist to provide a dose of, for example, from about 0.01 mg/m$^2$ to about 10 mg/m$^2$.

In some embodiments, the Cck1R agonist may be administered, for example, from a single dose to multiple doses per week, although in some embodiments the method can be performed by administering the Cck1R agonist at a frequency outside this range. In certain embodiments, the Cck1R agonist may be administered from about once per month to about five times per week.

TABLE 3

ATXN1 mouse cerebellar RNA-seq summary.

| Genotype | Disease Status | 5 weeks | 12 weeks | 28 weeks |
|---|---|---|---|---|
| wt/FVB RINs (RQS) | unaffected | 197** (8.1, 8.6, 8.0) | 44.5* 9.2, 9.1, 9.3 | 40.3* 9.2, 9.1, 9.2 |
| ATXN1[30Q] RQS | very mild | 188** (8.1, 8.1, 8.1) | ND | ND |
| ATXN1[82Q] | severe ataxia, | 190** | 61.1* | 27.5* |

TABLE 3-continued

ATXN1 mouse cerebellar RNA-seq summary.

| Genotype | Disease Status | 5 weeks | 12 weeks | 28 weeks |
|---|---|---|---|---|
| | progressive degeneration | | | |
| RINs (RQS) | | (8.3, 7.9, 8.4) | 9.0, 9.1, 9.2 | 8.9, 8.9, 9.0 |
| ATXN1[30Q] D776 | severe ataxia, non-progressive degeneration | 203** | 51.8* | 30.5* |
| RINs (RQS) | | (7.9, 7.9, 8.0) | 9.4, 9.2, 9.2 | 9.0, 9.0, 9.0 |

*sequences obtained using Illumina GAIIX
**sequences obtained using Illumina HiSeq 2000

TABLE 4

SCA1 WGCNA Magenta Module Gene List:
(Module correlation ≥9.0); Module overlaps; @ human cerebellar M6D (Oldham et al., 2008), # AOA2 Blue (Fogel et at., 2014), ✣ Purkinje cell enriched translation (Doyle et al., 2008)

1700018L02Rik
2310003H01Rik
2610203C20Rik
2700070H01Rik
2810456M11Rik
4930413G21Rik
6030419C18Rik(0.91305)
A330050F15Rik ✣
AK129341 ✣ (0.91934)
Ablim2
Adamts3
Ads1
Agfg2
Aif1 #
Aldh7a1
Aldh9a1(−0.90920)
Aldoc @#
Ankrd33b
Anks1b (0.90920)
Ano6 #
Antxr1 #
Ap4m1
Arap1
Arhgef2
Arhgef33 (0.96409)
Atf1
Atf2
Atp2a3 ✣ (0.97645)
B330016D10Rik
B3gnt2
Baiap2 #
Bcar1
Bcl10
Bcl11a ✣#
Bcl2l11
Bean1
Cacna1g @ ✣(0.96294)
Cacnb2
Cacng4
Calb1 @ ✣
Capn2
Car 7 ✣
Casp3 # (−0.9693)
Casq2 ✣
Ccdc120
Ccdc64
Ccnd1 ✣
Ccni
Cd70
Cdh1
Cdk16 (0.91184)
Cemip
Cep104
Cep72
Cep76 @
Cerk ✣ (0.97527)
Chst8 ✣
Clmn ✣
Cmtm3 #
Cnnm4
Cntnap5b
Colq #
Cox6b2 ✣
Crpeb1 ✣
Creg1 ✣#
Csad ✣
Cthrc1
Cttnbp2 (0.91102)
Cx3cr1
Cyth3
Dagla (0.92278)
Dand5
Dap ✣# (0.92109)
Dbndd1 (0.91162)
Ddx49
Dgkz ✣ (0.90376)
Dlg2 @
Dner ✣ (0.99296)
Doc2b (0.92012)
Dyrk3 ✣
Ebf2 ✣
Efna3
Eif1a
Eif2ak1 #
Eifak3
Eifn2
Enpp4
Ephb2
Eps8l2 ✣#
Etv4 (0.98068)
Exosc10
F2r ✣
Fam107b (0.90846)
Fam117a (0.96476)
Fam174b (0.91523)
Fam21
Fam222a
Far2
Fbxl22
Fgd3 (0.95765)
Fgfl1
Fgfl3 #
Fgf7 ✣(0.97522)
Gabbr1
Gain1
Garn13 ✣ (0.99013)
Gchfr ✣#
Gfap
Gja1
Gjb2
Gla
Gli1
Gm10190
Gm13944 (0.91219)
Gm16740
Gm4285
Gm9866
Gng13 @ (0.99148)
Golt1b
Gp1bb TABLE 4-continued SCA1 WGCNA Magenta Module Gene List:
(Module correlation ≥9.0); Module overlaps; @ human cerebellar M6D
(Oldham et al., 2008), # AOA2 Blue (Fogel et at., 2014), ✤
Purkinje cell enriched translation (Doyle et al., 2008)

Gpatch1
Gprc5b
Gria1 (0.93785)
Grid2 ✤
Grid2ip ✤
Grik1 ✤ (0.91039)
Grm8
Gsg1l #
Gskip
H2-D1 ✤
Hdc ✤#
Heatr5a
Hk2 (0.92884)
Homer3 @ (0.97704)
Hpca
Hpca 11 ✤
Hrh3
Hrk (−0.96849)
Hs6st1 #
Icmt @ ✤ (0.98091)
Id2 @ ✤ (0.93777)
Igfbp5 ✤
Iltifb
Imp4
Inpp4a1 ✤
Inpp5a @ ✤ (0.95307)
Ipo5
Itgbp1 ✤ (0.90136)
Itpka ✤ (0.98252)
Itpr1 ✤
Jun
Karin @ ✤
Kcna6
Kcnab1 (0.96063)
Kcng4 ✤
Kcnip1 ✤
Kcnmb4 ✤
Kcnq4
Kctd12 @ ✤ (0.91943)
Kdelc2
Kif1c
Kif5a
Kif10
Lancl1
Lhfpl2 #
Lhpp #
Lhx1os
Lhx5 ✤
Lix1
Lnx2
Lpcat1
Lrrfip1 (0.97372)
Lynx1
Mapk4
Mdfi
Medag
Mex3b
Mfsd12 #
Mmp23
Mpeg1
Mrps25
Mthfd11
Mthfsd
Mtss1 ✤
Mxi1l #
Mxra1 (−0.95863)
Mylip
Nab2 #

TABLE 4-continued

SCA1 WGCNA Magenta Module Gene List:
(Module correlation ≥9.0); Module overlaps; @ human cerebellar M6D
(Oldham et al., 2008), # AOA2 Blue (Fogel et at., 2014), ✤
Purkinje cell enriched translation (Doyle et al., 2008)

Nadsyn1
Nek2 ✤ (0.94733)
Neil1 (0.90093)
Neurod2
Nexn
Nkain1
Nkd1
Nign2
Nog (0.91352)
Npr1
Npy
Nr2f2
Nsg1 ✤ (0.94063)
Nfng1
Nfng2
Nup54
Nup93
Ociad2
Opn3 ✤
Orai2 (0.94352)
Ofud1
Padi1 (−0.97288)
Papss2
Pcdhgb5
Pcp4 @ (0.99485)
Pcsk6 ✤
Pde5a #
Pex26
Phactr3
Pkp3 ✤ (0.92159)
Plcb3 ✤
Plekhd1 (0.91650)
Pixdc1 @ ✤ (0.97619)
Poc1b #
Polr3k
Pou3f4
Ppapdc2 (0.95821)
Ppm1 ✤
Ppp1r16b ✤ (0.92773)
Ppp1r17 @ (0.93525)
Ppp1r1b #
Ppp1r3c
Ppp2r2a
Ppp4r4 (0.90671)
Prdm8
Prkcg
Prpf3
Psd2 ✤
Ptprm
Rab3d ✤
Rab43
Rab43
Rab6
Rasa1 (0.96549)
Rbm19
Rbm22
Rdh 11 ✤
Reep2
Reill1 (−0.93398)
Rgma #
Rgs8 ✤ (0.96501)
Rhobtb2 (0.93596)
Rhod
Rian
Rmdn3 (0.96671)
Rnf145 (0.91594)
Rnf157
Rnf19b
Rps6kc1
Rousd3
Rspo3

TABLE 4-continued

SCA1 WGCNA Magenta Module Gene List:
(Module correlation ≥9.0); Module overlaps; @ human cerebellar M6D
(Oldham et al., 2008), # AOA2 Blue (Fogel et at., 2014), ✣
Purkinje cell enriched translation (Doyle et al., 2008)

Rtei1 ✣
Ryr1 #
Samd8
Sbk1 ✣ (0.94506)
Scn1b
Sdc1 #
Sec61a1
Sema7a
Sept5
Sfxn1
Sh3glb2 #
Sh3pxd2b
Shabk2
Shisa6 (0.90648)
Slc16a10
Slc1a @ ✣
Slc20a1 @ ✣
Slc35c1
Slc35f4
Slc39a6
Slc41a3 ✣
Slc5a1 ✣
Slc6a6 ✣
Slc7a11
Slc9a3 ✣
Snx9
Soat1
Spag5 ✣ (0.90392)
Spns2
Sppl2b (0.94426)
St3gal5
St6gal1
Stac ✣ (0.94765)
Stap2
Stk17b
Strip2
Sulf1 #
Susd4
Synj2
Syt12 (−0.90945)
Taok3
Tbp11
Tcf7l1
Tex261 ✣#
Tm6sf1
Tmem200b (0.98649)
Tmem231
Tmem255a
Tmem41a ✣
Tmod1 l
Tmtc1
Tnc
Tob1
Tprkb
Trabd2b (0.97066)
Trim9b # (0.94599)
Trmt61a
Trp53bp2 (−0.91108)
Trpc3 @ ✣ (0.99098)
Tshz1
Tspan11 ✣ (0.93429)
Ttll3
Ttll5 ✣
Tuba8 ✣
Ubash3b (0.90785)
Uspl1
Utp23
Vgll4
Vimp
Vopp1
Vwa7 #
Wee1
Wiz ✣ (0.94114)
Wsb2
Ypel4
Ywhah @ (0.99048)
Zbtb40
Zdhhc14
Zfp346
Zfp385c
Zfp512
Zfp830

TABLE 5

Lt Yellow WGCNA module gene list

Alas1
Aldh1l1
Aldh1l2
Amotl2
Ank2
Arid5a
Bbc3
Clu
Fbxw17
Frat1
Gm11744
Hyi
Irx1
Jund
Limd2
Lingo4
Lpgat1
Luzp1
Ly6e
Metrnl
Mtfp1
Naprt1
Prdx6
Rbm28
Rp9
Rreb1
Sdc4
Sh2d3c
Slc12a6
Slc3a2
Trip10
Unc80
Wnt7b
Zbtb46
Zdhhc5

TABLE 6

Magenta Module Hub Gene Connectivity

| Gene | Intramodular Connectivity |
| --- | --- |
| Fam21 - Family sequence homology 21 | 50.512 |
| Stac - SH3 and cysteine rich domain | 48.269 |
| Innpp5a - Inositol polyphospate-5-phosphatase A | 47.498 |
| Trpc3 - Transient receptor potential cation channel, subfamily C, member 3 | 46.365 |

TABLE 6-continued

Magenta Module Hub Gene Connectivity

| Gene | Intramodular Connectivity |
|---|---|
| Fam107b - Family sequence homology 21, member B | 45.270 |
| Dner - Delta/notch-like EGF repeat containiing | 44.834 |
| Grik1 - Glutamate receptor, ionotropic, kainate 1 | 44.595 |
| Gabbr1 - GABA B receptor, 1 | 44.536 |
| Rgs8 - Regulator of G-protein signaling 8 | 44.355 |
| Homer3 - Homer homolog 3 | 43.294 |

TABLE 7

Ingenuity Pathway Analysis (IPA) Disease-Associated ATXN1 Cerebellar WGCNA Modules

| WGCNA Module | Top Upstream Regulators | p-Value | Top Canonical Pathways | p-value |
|---|---|---|---|---|
| Magenta | Atxn1 | 5.91e−08 | Synaptic LTD | 1.49e−5 |
| | Erbb2 | 3.97e−06 | GluR Signaling | 2.7e−04 |
| | Tgfb1 | 5.21e−08 | Dopamine-Darpp32 cAMP Signaling | 1.05e−03 |
| | Bdnf | 1.82e−06 | Hippo Signaling | 2.39e−03 |
| | | | Bladder Cancer | 2.53e−03 |
| Lt Yellow | JunD | 1.12e−04 | Planar Cell Polarity Signaling | 1.45e−04 |
| | Tert butyl hydroperoxide | 1.81e−04 | | |

TABLE 8

Cic binding motif - TGAATGGA

4930413G21Rik
5730422E09Rik
9530062K07Rik
Adamts3
Aldh9a1
Aldoc
Ankrd33b
Ano6
Antxr1
Arap1
Arhgef33
B330016D10Rik
B3gnt2
Cacna1g
Cacng4
Calb1
Ccdc115
Ccdc120
Ccnd1
Cd70
Cep104
Cep72
Cerk
Chst8
Cmtm3
Colq
Cox6b2
Cpeb1
Cthrc1
Cttnbp2
Enpp4
Ephb2

TABLE 8-continued

Cic binding motif - TGAATGGA

Etv4
Fam117a
Fam174b
Fam19a3
Fam21
Fam222a
Fgd3
Fgf11
G630025P09Rik
Gas8
Gjb2
Gla
Gm3230
Golt1b
Hk2
Hnrnph2
Homer3
Hpca
Id2
Imp4
Inca1
Inpp4a
Itpka
Jun
Kalrn
Kcna6
Kcnab1
Kcng4
Kcnip1
Kctd12
Kif1c
Kif5a
Lnx2
Lpcat1
Lsm7
Mapk4
Medag
Mfsd12
Mir5130
Mthfd1l
Mylip
Nadsyn1
Nek2
Nell1
Nexn
Nkd1
Nlgn2
Nr2f2
Nsg1
Ntng1
Ntng2
Opn3
Otud1
Padi2
Papss2
Pcdhgb5
Pcsk6
Pde5a
Pex26
Phactr3
Pkp3
Plxdc1
Polr1d
Ppapdc2
Ppm1j
Ppp4r4
Prkcg
Prmt8
Prpf3
Ptprm
Rab43
Rabl6
Rasal1
Rbbp6
Rdh11
Recql
Reep2
Rell1

TABLE 8-continued

Cic binding motif - TGAATGGA

Rgs8
Rhobtb2
Rian
Rps6kc1
Rpusd3
Scn1b
Sema7a
Sfxn1
Sh3pxd
Shisa6
Slc35c1
Slc41a3
Slc9a3
Snx9
Spag5
Spns2
Sppl2b
Strip2
Sulf1
Synj2
Tmem256
Tmem41a
Tmod1
Tmtc1
Trabd2b
Trmt61a
Trp53bp2
Trpc3
Tspan11
Tuba8
Ubash3b
Uspl1
Vimp
Vwa7
Wiz
Zbtb40
6030419C18Rik
A930001C03Rik
Ablim2
Aif1
Aldh9a1
Antxr1
Atf1
Atg2b
Atl2
B330016D10Rik
Cacng4
Calb1
Casp3
Ccdc115
Ccnd1
Cd70
Cdk16
Cemip
Cep104
Clmn
Cmtm3
Cox6b2
Cpsf3
Creg1
Cttnbp2
Dap
Deaf1
Dffb
Dhcr7
Eps8l2
Etv4
Exosc1
Fam107b
Fam117a
Fam174b
Far2
Fbxl22
Fgf11
G630025P09Rik
Galnt4
Gfap
Gjb2

TABLE 8-continued

Cic binding motif - TGAATGGA

Gla
Gm9866
Gsg1l
Gskip
H2-D1
H2-L
Heatr5a
Hnrnph2
Hrh3
Hrk
Igfbp5
Iltifb
Imp4
Inpp4a
Inpp5a
Ipo5
Itgb1bp1
Itpka
Kalrn
Kcnab1
Kcnip1
Kcnmb4
Lancl1
Lhpp
Lix1
Medag
Mex3b
Mpnd
Mtss1
Mxi1
Mxra7
Mylip
Nadsyn1
Neurod2
Nup93
Ociad2
Opn3
Padi2
Pcdhgb5
Pde5a
Poc1b
Polr3k
Pou3f4
Ppp4r4
Primpol
Rbm19
Rhod
Rnf157
Rnf19b
Sema7a
Sh3glb2
Sh3pxd2b
Slc1a6
Soat1
St6gal1
Stac
Stap2
Stk17b
Strip2
Sulf1
Syt13
Tbpl1
Tmtc1
Tnc
Tob1
Trim9
Tspan11
Wsb2
Zdhhc14
Zdhhc16
Zfp512

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Mice

The Institutional Animal Care and Use Committee approved all animal use protocols. All mice were housed and managed by Research Animal Resources under specific-pathogen-free (SPF) conditions in an AAALAC-approved facility. $Cck^{-/-}$, $Cck1R^{-/-}$ and $Cck2R^{-/-}$ mice were obtained from Jackson Labs, Bar Harbor, Me. ($Cck^{-/-}$; cat #017710/RRID: IMSR-JAX:017710, $Cck1R^{-/-}$; cat #006365/RRID: IMSR-JAX:006367 and $Cck2R^{-/-}$; cat #006365/RRID: IMSR-JAX:006369). In all experiments equal numbers of male and females were used.

RNA Isolation and Sequencing

Total RNA was isolated from dissected cerebella using TRIzol Reagent (Life Technologies, Inc., Carlsbad, Calif.) following the manufacturer's protocols. Cerebella were homogenized using an RNase-Free Disposable Pellet Pestles in a motorized chuck. For RNA-sequencing, RNA was further purified to remove any organic carryover using the RNeasy Mini Kit (Qiagen, Venlo, Netherlands) following the manufacturer's RNA Cleanup protocol.

Cerebellar RNA from three biological replicates/genotype was isolated. Purified RNA was sent to the University of Minnesota Genomics Center for quality control, including quantification using fluorimetry (RIBOGREEN assay, Life Technologies, Inc., Carlsbad, Calif.) and RNA integrity assessed with capillary electrophoresis (Agilent BioAnalyzer 2100, Agilent Technologies, Inc., Santa Clara, Calif.) generating an RNA integrity number (RIN). All submitted samples had greater than 1 μg total mass and RINs 7.9 or greater (Table 3). Library creation was completed using oligo-dT purification of polyadenylated RNA, which was reverse transcribed to cDNA. cDNA was fragmented, blunt-ended, and ligated to barcoded adaptors. Library was size selected to 320 bp+/−5% to produce average inserts of approximately 200 bp, and size distribution validated using capillary electrophoresis and quantified using fluorimetry (PICOGREEN, Life Technologies, Inc., Carlsbad, Calif.) and q-PCR. Libraries were normalized, pooled and sequenced. 12-week and 28-week ATXN1[82Q], ATXN1 [30Q]–D776, and wt/FVB samples were sequenced on an Illumina GAIIX using a 76 nt paired-end read strategy, while five-week samples from these genotypes were sequenced on a HiSeq 2000 (Illumina, Inc., San Diego, Calif.) using a 100 nt paired-end read strategy. Data were stored and maintained on University of Minnesota Supercomputing Institute (MSI) Server.

Reads were aligned to mouse reference genome mm10 with Tophat2 (Kim et al., 2013, *Genome Biology* 14:R36) using mostly default parameters with two exceptions: mate inner distance and standard deviation were adjusted to the data and using a gene annotation model only looking for supplied junctions (mm10 gtf file from iGenomes). Reads were quantified using Cuffquant (Trapnell et al., 2010, *Nat. Biotechnol.* 28:511-515; Roberts et al., 2011, *Genome Biology* 12:R22), and differential gene expression was determined with Cuffdiff2 using default parameters (Trapnell et al., 2012, *Nat Protoc.* 7:562-578). Genes/introns with a q≤0.05 were considered significant. Genome tracks were visualized with Integrated Genomics Viewer (Broad Institute). Results were graphed with CummeRbund (Goff et al., 2013). Pathway and clustering analysis was completed with Ingenuity Pathway Analysis (Ingenuity Systems, Redwood City, Calif.). Normalized expression values of all genes across all samples were prepared from Cuffquant results using Cuffnorm (Trapnell et al., 2010, *Nat. Biotechnol.* 28:511-515). The iGenomes mm10 gtf contains both miRNAs and snoRNAs, which are too small to be accurately sequenced using standard RNA-seq library preparation and sequencing. Including these short transcripts in the expression data used for the PCA resulted in Purkinje Cells driven by the extreme expression of a few miRNAs and snoRNAs. Expression data used in the PCA was re-quantified using Cuffquant and Cuffnorm after removing miRNAs and snoRNAs from the iGenomes gtf.

Expression Analyses

Gene expression analysis with the Tuxedo pipeline (Kim et al., 2013, *Genome Biology* 14:R36; Trapnell et al., 2010, *Nat. Biotechnol.* 28:511-515). Initial read quality was assessed using FastQC (Andrews-Babraham Bioinformatics, FastO|QC A quality control tool for high throughput sequence data) and reads trimmed to remove low quality 3' ends and adapter contamination using Trimmomatic (Bolger et al., 2014, *Bioinformatics* btu170).

Reads were aligned to mouse reference genome mm10 with Tophat2 (Kim et al., 2013, *Genome Biology* 14:R36) using mostly default parameters with two exceptions: mate inner distance and standard deviation were adjusted to the data and using a gene annotation model only looking for supplied junctions (mm10 gtf file from iGenomes). Reads were quantified using Cuffquant (Trapnell et al., 2010, *Nat. Biotechnol.* 28:511-515; Roberts et al., 2011, *Genome Biology* 12:R22), and differential gene expression was determined with Cuffdiff2 using default parameters (Trapnell et al., 2012, *Nat Protoc.* 7:562-578). Genes/introns with a q≤0.05 were considered significant. Genome tracks were visualized with Integrated Genomics Viewer (Broad Institute). Results were graphed with CummeRbund (Goff et al., 2013). Pathway and clustering analysis was completed with Ingenuity Pathway Analysis (Ingenuity Systems, Redwood City, Calif.). Normalized expression values of all genes across all samples were prepared from Cuffquant results using Cuffnorm (Trapnell et al., 2010, *Nat. Biotechnol.* 28:511-515). The iGenomes mm10 gtf contains both miRNAs and snoRNAs, which are too small to be accurately sequenced using standard RNA-seq library preparation and sequencing. Including these short transcripts in the expression data used for the PCA resulted in Purkinje Cells driven by the extreme expression of a few miRNAs and snoRNAs. As a result, the expression data used in the PCA was re-quantified using Cuffquant and Cuffnorm after removing miRNAs and snoRNAs from the iGenomes gtf.

WGCNA

FPKM abundance estimates for all 27 samples were produced by CuffNorm (Trapnell et al., 2012, *Nat Protoc.* 7:562-578) and were log$_2$ transformed (log$_2$(FPKM+1)) for WGCNA analysis (Langfelder and Horvath, 2008, *BMC Bioinformatics* 9:559). The WGCNA R package (v. 1.41) was used to construct an unsigned gene coexpression network with a soft threshold power [beta] of 10. Nineteen modules were detected, including two that were significantly associated with ataxia (wt vs ATXN1[82Q] and ATXN1 [30Q]D776 mice, t-test, Bonferroni corrected p-value<1× 10$^{-5}$). Data for Magenta and Lt Yellow modules was exported to Cytoscape for visualization. Network figures are limited to the top 20% of genes with the strongest network connections—i.e., the topological overlap threshold was raised until only 20% of genes remained. The network modules are color coded by the differential expression at week 12 as follows: green: significantly downregulated in B05 compared to FVB and in D30 compared to FVB; red: significantly upregulated in B05 compared to FVB and in D30 compared to FVB; gray: either not significant in either or both of the two comparisons, or the direction is different between the two (e.g. up in B05 compared to FVB but down in D30 compared to FVB, or vice versa). The size of the circles is scaled by the absolute value of the mean log 2 fold change between B05 and FVB, and between D30 and FVB.

Genes that had a correlation of 0.9 or greater with the Magenta Module eigengene values for the ATXN1[82Q] mice across all time points (9 data points) were identified as genes in the Magenta Module that correlated with the sickest mice.

The genes in the Magenta and Lt Yellow modules were compared to modules from other published WGCNA analyses as previously described (Oldham et al., 2008, *Nat. Neurosci.* 11:1271-1282).

Histology and Immunostaining

Animals were anesthetized and transcardially exsanguinated with PBS (pH 7.4) and perfused using 10% formalin (30 mL). Brains were post-fixed overnight in 10% formalin and placed in PBS at 4° C. before sectioning. Cerebella were sectioned into 50 μm sagittal sections using a vibratome. Epitopes were exposed using antigen retrieval by boiling sections four times for 10 seconds each in 0.01M urea. Sections were blocked overnight in 2% normal donkey serum and 0.3% Triton X-100 in PBS. Subsequent staining was carried out in 2% normal donkey serum and 0.3% Triton X-100 in PBS. Anti-calbindin antibodies used were (Cat #C9848/RRID:AB-10115846, Sigma-Aldrich, St. Louis, Mo.) and rabbit (Cat #C2724/RRID:AB-258818, Sigma-Aldrich, St. Louis, Mo.) at a 1:250 dilution.

Sections were incubated for 24 hours with primary antibodies at 4° C. Following incubation, sections were washed three times in PBS and exposed to secondary antibodies (Alexa Fluor 488 antimuse-cat #715-546/RRID:AB-2340850 and Alexa Fluor 647 antirabbit-cat #711-605-152/ RRID:AB-2492288}, Jackson Immunoresearch Laboratories, Inc., West Grove, Pa.) for 24 hours at 4° C. Sections were washed three times in PBS and mounted onto charged slides (Colorfrost Plus, Thermo Fisher Scientific, Waltham, Mass.). Fluorescently labeled tissue was imaged using a confocal Olympus 1000 IX inverted microscope.

Example 2

Mice

The Institutional Animal Care and Use Committee approved all animal use protocols. All mice were housed and managed by Research Animal Resources under SPF conditions in an AAALAC-approved facility. For all experiments, an equal number of male and female mice were used.

Agonist Treatments

The Cck1 receptor (Cck1R) agonist A71623 (Tocris Bioscience, Bristol, United Kingdom) was resuspended in 20 mM PBS according to the manufacturer's directions. For the experiment with ATXN1[30Q]D776;Cck$^{-/-}$ (D30;Cck$^{-/-}$, FIG. 13) mice, osmotic minipumps (AZLET, Durect Corp., Cupertino, Calif.) containing either A71623 (1 mg/kg/day) or Vehicle (20 mM PBS) were implanted intraperitoneally in six-week-old mice. For the duration of the experiment, pumps were removed and replaced every seven weeks. Behavioral data was collected at the time points indicated in FIG. 13A. Because of the size of the osmotic minipumps, the mice have to be approximately 20 g or larger for safe implantation into the intraperitoneal space. In ATXN1[82Q] mice, single bolus injections of A71623 (19 mg/kg) or Vehicle were administered daily beginning at week 5 and continuing until the mice were approximately 20 g (for approximately seven days, or until the mice were 6 weeks old). At this time the pumps were implanted for the remainder of the experimental timeline.

Behavioral Tests

Rotarod

An accelerating rotarod was used to assess motor performance and learning. Mice were placed on a rotating rod (3 cm diameter) for four trials per day for four consecutive days. Each trial lasted a maximum of five minutes, during which time the rotating rod underwent linear acceleration from 4 to 40 rpm over the entire five minutes. Animals were scored for their latency to fall (in seconds) for each trial. Mice rested a minimum of 10 minutes in between each trial to avoid fatigue. Data were analyzed using a Two-Way ANOVA and Tukey post-hoc test for multiple comparisons that factors in day and genotype. Data presented in FIG. 13 and FIG. 14 represent Day 4 of testing for each time point.

Balance Beam/Bar Cross Test

The balance beam tests for balance and motor coordination. The apparatus consists of a linear, horizontal beam that is 3 feet in length and hangs 19 inches above the table. At the end of the beam opposite the starting point there is a safety box, which is a dark, enclosed structure measuring 7.5×7.5×5.5 inches that is accessible from the end of the balance beam. The beam is marked at four inches from both the beginning and the end to indicate start and stop lines that are used to determine time it takes to cross the beam. The baseline test occurs over four consecutive days: the first three days are training days and the fourth is a testing day. During the training days, naïve mice were run for four trials per day on the 15 mm wide square beam (data not shown). Prior to the first trial on each training day, each mouse was placed in the safety box to acclimate for 30 seconds. Both time to cross (in seconds) and the total number of foot slips were recorded for each trial. Time to cross is defined as the time from when the animal's hind legs cross the starting line to when their hind legs cross the finish line. Foot slips are defined as any time either of the hind paws unexpectedly slips off the beam. To reduce the impact of learning, only two training days were run for all non-nave animals following the baseline experiments.

On the test day, animals underwent two trials on each of six beams, ranging in order from easy (large) to difficult (small): 25 mm wide square, 27 mm diameter round, 15 mm wide square (training beam), 17 mm diameter round, 8 mm wide square, and 10 mm diameter round. As during the training trials, latency and the number of foot slips per trial were recorded. Tests were performed between 9 A.M. and 4 P.M.

For each mouse, the average time to cross and the average number of foot slips per beam on test day were determined. Test time to cross and foot slips were compared using a Two-Way repeated measures ANOVA and Tukey post-hoc test for multiple comparisons. Data presented in FIG. 13 and FIG. 14 represent the time to cross and number of foot slips recorded on the smallest beam (10 mm round) on test day.

Histology and Pathology

Animals were anesthetized and the cerebella rapidly removed. Half of the cerebellum was post-fixed overnight in 10% formalin and placed in PBS at 4° C. before sectioning. The other half was snap-frozen in liquid nitrogen for western blotting experiments. Fixed cerebella were sectioned into 50 µm sagittal sections using a vibratome. Epitopes were exposed using antigen retrieval by boiling sections three times for 15 seconds each in 0.01 M urea. Sections were blocked overnight in 2% normal donkey serum and 0.3% Triton X-100 in PBS. Subsequent staining was carried out in 2% normal donkey serum and 0.3% Triton X-100 in PBS. Anti-calbindin antibodies used were mouse (Cat #C9848/RRID:AB-10115846, Sigma-Aldrich, St. Louis, Mo.) and rabbit (Cat #C2724/RRID:AB-258818, Sigma-Aldrich, St. Louis, Mo.) at a 1:250 dilution. Sections were incubated for 24 hours with primary antibodies at 4° C. Following incubation, sections were washed three times in PBS and exposed to secondary antibodies (Alexa Fluor 488 anti-mouse-cat #715-546/RRID:AB-2340850 and Alexa Fluor 647 antirabbit-cat #711-605-152/RRID:AB-2492288, Jackson Immunoresearch Laboratories, Inc., West Grove, Pa.) for 24 hours at 4° C. Sections were washed three times in PBS and mounted onto charged slides (Colorfrost Plus, Fisher, Waltham, Mass.). Fluorescently labeled tissue was imaged using a confocal Olympus 1000 IX inverted microscope.

Molecular layer thickness was measured using the Olympus Fluoview imaging software. 20 µm-thick z-stack images were taken of the cerebellar primary fissure at 20×. A ruler was drawn from the leading edge of the primary fissure along the visible length. Six measurements, three on each side, were taken of the molecular layer from the base of the Purkinje Cell to the edge of the pial surface. At least three cerebellar sections per animal were measured this way, and averaged.

Western Blotting

Frozen cerebella were homogenized in standard Tris triton lysis buffer containing protease (Roche Molecular Systems, Inc., Indianapolis, Ind.) and phosphatase (Sigma-Aldrich, St. Louis, Mo.) inhibitors, then underwent three free/thaw cycles between liquid nitrogen and a 37° C. water bath. The samples were spun at 10,000 RPM for 10 minutes at 4° C., then the pellet was discarded. A Bradford assay (Bio-Rad Laboratories, Inc., Hercules, Calif.) was performed to determine protein concentration, and 30 µg of protein per sample was loaded onto a 4-20% gradient gel. The gels were run for 1-1.5 hours at 125V and then transferred onto nitrocellulose membranes using the TRANS-BLOT TURBO transfer system (Bio-Rad Laboratories, Inc., Hercules, Calif.). Membranes were incubated for 10 min at room temperature in blocking solution (1×PBS, 0.01% Tween20, 5% BSA). Membranes were incubated overnight at 4° C. with anti-P-ERK1/2 antibody (Cell Signaling Technology, Inc., Danvers, Mass.; 1:1000) in blocking solution. They were then washed 3× with 1×PBS and 0.01% Tween20. Chemiluminescent detection was performed by bathing the membrane in Super Signald West Pico Luminol (Thermo Fisher Scientific, Inc., Waltham, Mass.), then imaged using the ImageQuant LAS 4000 (GE Healthcare, Lifesciences) and densitometry analysis is performed using the ImageQuant Software (GE Healthcare, Life Sciences, Pittsburgh, Pa.). Once an image is obtained, the membrane was stripped using Restore Western Blot Stripping Buffer (Thermo Fisher Scientific, Inc., Waltham, Mass.). It was then washed three times for 10 minutes each wash in 1×PBS with 0.01% Tween20, and incubated again overnight in anti-total ERK1/2 (Cell Signaling Technology, Inc., Danvers, Mass.; 1:1000) in blocking buffer. Detection was again performed as described above.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for treating a subject having, or at risk of having, ataxia, the method comprising:
   administering to the subject having, or at risk of having, ataxia an amount of a composition comprising a cholecystokinin receptor (Cck1R) agonist effective to ameliorate at least one symptom or clinical sign of ataxia.

2. The method of claim 1 wherein the Cck1R agonist is A71623.

3. The method of claim 2 wherein A71623 is administered to the subject to provide a dose of at least 20 μg/kg/day.

4. The method of claim 3 wherein the dose of A71623 is 1 mg/kg/day.

5. The method of claim 1 wherein the Cck1R agonist is rebamipide.

* * * * *